(12) United States Patent
Anderson et al.

(10) Patent No.: US 9,560,846 B2
(45) Date of Patent: Feb. 7, 2017

(54) SYSTEM FOR HYPOTHERMIC TRANSPORT OF BIOLOGICAL SAMPLES

(75) Inventors: Lisa Maria Anderson, Boston, MA (US); Jared Alden Judson, Medford, MA (US); William Edelman, Sharon, MA (US)

(73) Assignee: Paragonix Technologies, Inc., Braintree, MA (US)

( * ) Notice: Subject to any disclaimer, the term of this patent is extended or adjusted under 35 U.S.C. 154(b) by 659 days.

(21) Appl. No.: 13/572,327

(22) Filed: Aug. 10, 2012

(65) Prior Publication Data

US 2014/0041403 A1    Feb. 13, 2014

(51) Int. Cl.
| | |
|---|---|
| *F25D 3/08* | (2006.01) |
| *F17C 13/00* | (2006.01) |
| *F25B 21/00* | (2006.01) |
| *G01K 13/00* | (2006.01) |
| *A01N 1/02* | (2006.01) |

(52) U.S. Cl.
CPC .................................. *A01N 1/0247* (2013.01)

(58) Field of Classification Search
CPC .................................................. A01N 1/0247
USPC ............ 62/457.1, 457.2, 457.9; 435/1.1–1.3, 435/283.1, 284.1
See application file for complete search history.

(56) References Cited

U.S. PATENT DOCUMENTS

| | | |
|---|---|---|
| 3,607,646 A | 9/1971 | de Roissart |
| 4,336,248 A | 6/1982 | Bonhard et al. |
| 4,575,498 A | 3/1986 | Holmes et al. |
| 4,952,409 A | 8/1990 | Bando et al. |
| 5,066,578 A | 11/1991 | Wikman-Coffelt |
| 5,149,321 A | 9/1992 | Klatz et al. |
| 5,234,405 A | 8/1993 | Klatz et al. |
| RE34,387 E | 9/1993 | Holmes et al. |
| 5,252,537 A | 10/1993 | De Winter-Scailteur |
| 5,320,846 A | 6/1994 | Bistrian et al. |
| 5,326,706 A | 7/1994 | Yland et al. |
| 5,356,771 A | 10/1994 | O'Dell |
| 5,362,622 A | 11/1994 | O'Dell et al. |
| 5,385,821 A | 1/1995 | O'Dell et al. |
| 5,395,314 A | 3/1995 | Klatz et al. |
| 5,434,045 A | 7/1995 | Jost |

(Continued)

FOREIGN PATENT DOCUMENTS

| | | |
|---|---|---|
| CA | 2722615 A1 | 10/2009 |
| CN | 101322861 A | 12/2008 |

(Continued)

OTHER PUBLICATIONS

International Preliminary Report on Patentability for PCT Application No. PCT/US2009/041274.

(Continued)

*Primary Examiner* — Ryan J Walters
*Assistant Examiner* — Joseph Trpisovsky
(74) *Attorney, Agent, or Firm* — Brown Rudnick LLP

(57) ABSTRACT

A system for the hypothermic (2-8° C.) transport of biological samples, such as tissues, organs, or body fluids. The system includes a first transport container to suspend the sample in preservation fluid and provides an ability to monitor the temperature of the sample. The first transport container, holding the sample, is placed in an insulated second transport container having a cooling medium. When assembled, the system allows for transport of biological samples for extended periods of time at a stable temperature.

20 Claims, 10 Drawing Sheets

(56) References Cited

U.S. PATENT DOCUMENTS

| | | |
|---|---|---|
| 5,584,804 A | 12/1996 | Klatz et al. |
| 5,586,438 A * | 12/1996 | Fahy .................................. 62/78 |
| 5,599,659 A | 2/1997 | Brasile et al. |
| 5,601,972 A | 2/1997 | Meryman |
| 5,629,145 A | 5/1997 | Meryman |
| 5,643,712 A | 7/1997 | Brasile |
| 5,656,154 A | 8/1997 | Meryman |
| 5,696,152 A | 12/1997 | Southard |
| 5,699,793 A | 12/1997 | Brasile |
| 5,702,881 A | 12/1997 | Brasile et al. |
| 5,707,971 A | 1/1998 | Fahy |
| 5,709,654 A | 1/1998 | Klatz et al. |
| 5,712,084 A | 1/1998 | Osgood |
| 5,716,378 A | 2/1998 | Minten |
| 5,752,929 A | 5/1998 | Klatz et al. |
| 5,827,222 A | 10/1998 | Klatz et al. |
| 5,843,024 A | 12/1998 | Brasile |
| 5,916,800 A | 6/1999 | Elizondo et al. |
| 5,922,598 A | 7/1999 | Mintchev |
| 5,963,335 A | 10/1999 | Boutelle |
| 5,965,433 A | 10/1999 | Gardetto et al. |
| 6,014,864 A | 1/2000 | Owen |
| 6,020,575 A | 2/2000 | Nagle et al. |
| 6,024,698 A | 2/2000 | Brasile |
| 6,046,046 A | 4/2000 | Hassanein |
| 6,060,232 A | 5/2000 | Von Baeyer et al. |
| 6,100,082 A | 8/2000 | Hassanein |
| 6,174,719 B1 | 1/2001 | Elizondo et al. |
| 6,194,137 B1 | 2/2001 | Khirabadi et al. |
| 6,209,343 B1 | 4/2001 | Owen |
| 6,241,945 B1 | 6/2001 | Owen |
| 6,280,925 B1 | 8/2001 | Brockbank |
| 6,303,388 B1 | 10/2001 | Fahy |
| D453,828 S | 2/2002 | Brassil et al. |
| 6,375,613 B1 | 4/2002 | Brasile |
| 6,406,839 B1 | 6/2002 | Segall et al. |
| 6,475,716 B1 | 11/2002 | Seki |
| 6,485,450 B1 | 11/2002 | Owen |
| 6,492,103 B1 | 12/2002 | Taylor |
| D468,436 S | 1/2003 | Brassil et al. |
| D470,594 S | 2/2003 | Brassil et al. |
| 6,569,615 B1 | 5/2003 | Thatte et al. |
| 6,582,953 B2 | 6/2003 | Brasile |
| 6,596,531 B2 | 7/2003 | Campbell et al. |
| 6,642,019 B1 | 11/2003 | Anderson et al. |
| 6,642,045 B1 | 11/2003 | Brasile |
| 6,656,380 B2 | 12/2003 | Wood et al. |
| 6,673,008 B1 | 1/2004 | Thompson et al. |
| 6,673,594 B1 | 1/2004 | Owen et al. |
| 6,677,150 B2 | 1/2004 | Alford et al. |
| 6,699,231 B1 | 3/2004 | Sterman et al. |
| 6,740,484 B1 | 5/2004 | Khirabadi et al. |
| 6,773,877 B2 | 8/2004 | Fahy |
| 6,794,124 B2 | 9/2004 | Steen |
| 6,794,182 B2 | 9/2004 | Wolf, Jr. |
| 6,905,871 B1 | 6/2005 | Doorschodt et al. |
| 6,924,267 B2 | 8/2005 | Daemen et al. |
| 6,953,655 B1 | 10/2005 | Hassanein et al. |
| 6,977,140 B1 | 12/2005 | Owen et al. |
| 6,994,954 B2 | 2/2006 | Taylor |
| 7,005,253 B2 | 2/2006 | Polyak et al. |
| 7,008,535 B1 | 3/2006 | Spears et al. |
| 7,029,839 B2 | 4/2006 | Toledo-Pereyra et al. |
| D531,319 S | 10/2006 | Schein et al. |
| D531,320 S | 10/2006 | Garland et al. |
| 7,157,222 B2 | 1/2007 | Khirabadi et al. |
| 7,176,015 B2 | 2/2007 | Alford et al. |
| 7,270,946 B2 | 9/2007 | Brockbank et al. |
| 7,294,278 B2 | 11/2007 | Spears et al. |
| 7,316,922 B2 | 1/2008 | Streeter |
| 7,326,564 B2 | 2/2008 | Lundell et al. |
| 7,361,365 B2 | 4/2008 | Birkett et al. |
| 7,410,474 B1 | 8/2008 | Friend et al. |
| 7,504,201 B2 | 3/2009 | Taylor et al. |
| 7,572,622 B2 | 8/2009 | Hassanein et al. |
| 7,651,835 B2 | 1/2010 | Hassanein et al. |
| 7,678,563 B2 * | 3/2010 | Wright et al. ............. 435/284.1 |
| 7,691,622 B2 | 4/2010 | Garland et al. |
| 7,749,693 B2 | 7/2010 | Brassil et al. |
| 7,811,808 B2 | 10/2010 | van der Plaats et al. |
| 7,824,848 B2 | 11/2010 | Owen et al. |
| 7,897,327 B2 | 3/2011 | Millis et al. |
| 8,097,449 B2 | 1/2012 | Garland et al. |
| 8,268,547 B2 | 9/2012 | Owen et al. |
| 8,268,612 B2 | 9/2012 | Owen et al. |
| 8,304,181 B2 * | 11/2012 | Hassanein et al. ............ 435/1.1 |
| 8,420,380 B2 | 4/2013 | Fishman et al. |
| 8,465,970 B2 | 6/2013 | Hassanein et al. |
| 2002/0042131 A1 | 4/2002 | Brockbank et al. |
| 2002/0051779 A1 | 5/2002 | Gage et al. |
| 2002/0064768 A1 | 5/2002 | Polyak et al. |
| 2002/0068360 A1 | 6/2002 | Brockbank et al. |
| 2002/0115634 A1 | 8/2002 | Polyak et al. |
| 2002/0177117 A1 | 11/2002 | Wolf |
| 2003/0022148 A1 | 1/2003 | Seki |
| 2003/0053998 A1 | 3/2003 | Daemen et al. |
| 2003/0118980 A1 | 6/2003 | Taylor |
| 2003/0125804 A1 | 7/2003 | Kruse et al. |
| 2003/0180704 A1 | 9/2003 | Brockbank et al. |
| 2004/0014199 A1 | 1/2004 | Streeter |
| 2004/0038192 A1 | 2/2004 | Brasile |
| 2004/0038193 A1 | 2/2004 | Brasile |
| 2004/0058432 A1 | 3/2004 | Owen et al. |
| 2004/0067480 A1 | 4/2004 | Brockbank et al. |
| 2004/0111104 A1 | 6/2004 | Schein et al. |
| 2004/0170950 A1 | 9/2004 | Prien |
| 2004/0171138 A1 * | 9/2004 | Hassanein et al. ........ 435/284.1 |
| 2004/0221719 A1 | 11/2004 | Wright et al. |
| 2004/0224298 A1 | 11/2004 | Brassil et al. |
| 2004/0224299 A1 | 11/2004 | Garland et al. |
| 2004/0241634 A1 | 12/2004 | Millis et al. |
| 2004/0248281 A1 | 12/2004 | Wright et al. |
| 2005/0100876 A1 | 5/2005 | Khirabadi et al. |
| 2005/0147958 A1 | 7/2005 | Hassanein et al. |
| 2005/0153271 A1 * | 7/2005 | Wenrich ......................... 435/1.1 |
| 2005/0221269 A1 | 10/2005 | Taylor et al. |
| 2005/0233299 A1 | 10/2005 | Sawa et al. |
| 2005/0255442 A1 | 11/2005 | Brassil et al. |
| 2005/0277106 A1 | 12/2005 | Daemen et al. |
| 2006/0019388 A1 | 1/2006 | Hutmacher et al. |
| 2006/0063142 A1 | 3/2006 | Owen et al. |
| 2006/0121439 A1 | 6/2006 | Baker |
| 2006/0121512 A1 | 6/2006 | Parenteau |
| 2006/0121605 A1 | 6/2006 | Parenteau |
| 2006/0141077 A1 | 6/2006 | Pettersson |
| 2006/0148062 A1 | 7/2006 | Hassanein et al. |
| 2006/0154357 A1 | 7/2006 | Hassanein et al. |
| 2006/0154358 A1 | 7/2006 | Hassanein et al. |
| 2006/0154359 A1 | 7/2006 | Hassanein et al. |
| 2006/0160204 A1 | 7/2006 | Hassanein et al. |
| 2006/0208881 A1 * | 9/2006 | Suzuki ..................... 340/539.27 |
| 2006/0292544 A1 | 12/2006 | Hassanein et al. |
| 2007/0009881 A1 | 1/2007 | Arzt et al. |
| 2007/0015131 A1 | 1/2007 | Arzt et al. |
| 2007/0166292 A1 | 7/2007 | Brasile |
| 2007/0184545 A1 | 8/2007 | Plaats et al. |
| 2007/0190636 A1 | 8/2007 | Hassanein et al. |
| 2007/0243518 A1 | 10/2007 | Serna et al. |
| 2007/0275364 A1 | 11/2007 | Hassanein et al. |
| 2008/0017194 A1 | 1/2008 | Hassanein et al. |
| 2008/0070229 A1 | 3/2008 | Streeter |
| 2008/0070302 A1 | 3/2008 | Brockbank et al. |
| 2008/0096184 A1 | 4/2008 | Brasile |
| 2008/0145919 A1 | 6/2008 | Franklin et al. |
| 2008/0187901 A1 | 8/2008 | Doorschodt et al. |
| 2008/0234768 A1 | 9/2008 | Hassanein et al. |
| 2008/0286747 A1 | 11/2008 | Curtis et al. |
| 2008/0288399 A1 | 11/2008 | Curtis et al. |
| 2008/0311552 A1 | 12/2008 | Min |
| 2009/0197240 A1 | 8/2009 | Fishman et al. |
| 2009/0197241 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |

(56) References Cited

U.S. PATENT DOCUMENTS

| | | |
|---|---|---|
| 2009/0226878 A1 | 9/2009 | Taylor et al. |
| 2009/0291486 A1 | 11/2009 | Wenrich |
| 2010/0015592 A1 | 1/2010 | Doorschodt |
| 2010/0028850 A1 | 2/2010 | Brassil |
| 2010/0086907 A1* | 4/2010 | Bunegin et al. ............... 435/1.1 |
| 2010/0112542 A1 | 5/2010 | Wright et al. |
| 2010/0151559 A1 | 6/2010 | Garland et al. |
| 2010/0209902 A1 | 8/2010 | Zal et al. |
| 2010/0216110 A1 | 8/2010 | Brockbank |
| 2010/0221696 A1 | 9/2010 | Owen et al. |
| 2010/0233670 A1 | 9/2010 | Gavish |
| 2010/0234928 A1 | 9/2010 | Rakhorst et al. |
| 2011/0033916 A1 | 2/2011 | Hutzenlaub et al. |
| 2011/0039253 A1 | 2/2011 | Owen et al. |
| 2011/0053256 A1 | 3/2011 | Owen et al. |
| 2011/0059429 A1 | 3/2011 | Owen et al. |
| 2011/0129810 A1 | 6/2011 | Owen et al. |
| 2011/0129908 A1 | 6/2011 | Owen et al. |
| 2011/0136096 A1 | 6/2011 | Hassanein et al. |
| 2011/0183310 A1 | 7/2011 | Kravitz et al. |
| 2011/0212431 A1 | 9/2011 | Bunegin et al. |
| 2011/0217689 A1 | 9/2011 | Bunegin et al. |
| 2012/0148542 A1 | 6/2012 | Kravitz |

FOREIGN PATENT DOCUMENTS

| | | |
|---|---|---|
| DE | 19922310 A1 | 11/2000 |
| DE | 102005048625 A1 | 4/2007 |
| EP | 2278874 A1 | 2/2011 |
| EP | 2480069 A1 | 8/2012 |
| JP | 8169801 A | 7/1996 |
| JP | 2008120713 A | 5/2008 |
| WO | 9743899 A1 | 11/1997 |
| WO | 0018225 A1 | 4/2000 |
| WO | 0018226 A2 | 4/2000 |
| WO | 0060935 A1 | 10/2000 |
| WO | 0137719 A2 | 5/2001 |
| WO | 0154495 A1 | 8/2001 |
| WO | 0178504 A2 | 10/2001 |
| WO | 0178505 A1 | 10/2001 |
| WO | 0195717 A2 | 12/2001 |
| WO | 0217714 A2 | 3/2002 |
| WO | 0226034 A2 | 4/2002 |
| WO | 0232225 A2 | 4/2002 |
| WO | 02089571 A1 | 11/2002 |
| WO | 2004017838 A2 | 3/2004 |
| WO | 2004026031 A2 | 4/2004 |
| WO | 2004052101 A1 | 6/2004 |
| WO | 2004089085 A2 | 10/2004 |
| WO | 2004089090 A1 | 10/2004 |
| WO | 2004105484 A1 | 12/2004 |
| WO | 2004110146 A1 | 12/2004 |
| WO | 2005022994 A1 | 3/2005 |
| WO | 2005074681 A2 | 8/2005 |
| WO | 2005099588 A2 | 10/2005 |
| WO | 2006033674 A1 | 3/2006 |
| WO | 2006042138 A2 | 4/2006 |
| WO | 2006052133 A2 | 5/2006 |
| WO | 2006060709 A2 | 6/2006 |
| WO | 2007111495 A1 | 10/2007 |
| WO | 2007124044 A2 | 11/2007 |
| WO | 2008108996 A1 | 9/2008 |
| WO | 2008144021 A2 | 11/2008 |
| WO | 2008150587 A2 | 12/2008 |
| WO | 2009020412 A1 | 2/2009 |
| WO | 2009041806 A1 | 4/2009 |
| WO | 2009099939 A2 | 8/2009 |
| WO | 2009132018 A1 | 10/2009 |
| WO | 2010096821 A2 | 8/2010 |
| WO | 2011038251 A1 | 3/2011 |

OTHER PUBLICATIONS

Search Report for PCT Application No. PCT/US2009/041274.
Bunegin, et al., The Application of Fluidics Based Technology for Perfusion Preservation of Adult, Human Sized, Canine Hearts, from the Department of Anesthesiology, Health Science Center at San Antonio, University of Texas, vol. 8, No. 1/2 (2003), pp. 73-78.
Bunegin, et al., The Application of Fluidics Technology for Organ Preservation, Biomedical Instrumentation & Technology, Mar./Apr. 2004, pp. 155-164.
Bunegin, et al., Interstitial pO2 and High Energy Phosphates in the Canine Heart during Hypothermic Preservation in a New, Portable, Pulsatile Perfusion Device, from the Department of Anesthesiology University of Texas Health Science Center at San Antonio, Texas; and Center for Cardiovascular Surgery of the Republic of Lithuania, Vilnius, Lithuania, vol. 3, No. 3, Oct. 1998, pp. 1-6.
Calhoon, et al., Twelve-Hour Canine Heart Preservation With a Simple, Portable Hypothermic Organ Perfusion Device, Ann Thorac Surg 1996;62:91-3.
Steinbrook, The New England Journal of Medicine, Organ Donation after Cardiac Death, Jul. 19, 2007.
Tolstykh, et al., Perfusion Preservation of Rodent Kidneys in a Portable Preservation Device Based on Fluidics Technology, vol. 73, 1508-1526, No. 9, May 15, 2002.
Tolstykh, et al., Novel portable hypothermic pulsatile perfusion preservation technology: Improved viability and function of rodent and canine kidneys, Ann Transplant, 2010; 15(3):1-9.
Wandall, et al., Galactosylation does not prevent the rapid clearance of long-term 40C-stored platelets, Blood, 2008; 111(6):3249-3256.
Weegman, et al., Continuous Real-time Viability Assessment of Kidneys Based on Oxygen Consumption, Transplant Proc. 2010; 42(6): 2020-2023.
LifePort Brochure, Organ Recovery Systems, www.organ-recovery.com.
http://organtransportsystems.com/index.html.
http://www.organ-recovery.com/home.php.
U.S. Appl. No. 13/420,962, filed Mar. 15, 2012, Apparatus for Oxygenation and Perfusion of Tissue for Organ Preservation, Maier and Judson.
U.S. Appl. No. 13/572,315, filed Aug. 10, 2012, System for Hypothermic Transport of Samples, Anderson (née Maier) and Judson.
U.S. Appl. No. 13/572,323, filed Aug. 10, 2012, Methods and Devices for Preserving Tissues, Anderson (née Maier) and Judson.
U.S. Appl. No. 13/572,332, filed Aug. 10, 2012, Methods and Systems for Assessing Ex-Vivo Organ Health, Anderson (née Maier) and Judson.
U.S. Appl. No. 13/572,341, filed Aug. 10, 2012, Storage and Preservation of Body Fluids, Anderson (née Maier), Judson, and Edelman.
Search Report and Written Opinion for PCT Application No. PCT/US2010/050230.

* cited by examiner

SYSTEM FOR HYPOTHERMIC TRANSPORT OF BIOLOGICAL SAMPLES

FIELD OF THE INVENTION

The invention relates to systems and method for hypothermic transport of biological samples, for example tissues for donation. The systems and methods provide a secure, sterile, and temperature-controlled environment for transporting the samples

BACKGROUND

There is a critical shortage of donor organs. Hundreds of lives could be saved each day if more organs (heart, kidney, lung, etc.) were available for transplant. While the shortage is partly due to a lack of donors, there is a need for better methods of preserving and transporting donated organs. Current storage and preservation methods allow only small time windows between harvest and transplant, typically on the order of hours. These time windows dictate who is eligible to donate organs and who is eligible to receive the donated organs. These time windows also result in eligible organs going unused because they cannot be transported to a recipient in time.

The transport window is most acute for heart transplants. Current procedures dictate that hearts cannot be transplanted after four hours of ischemia (lack of blood supply). Because of this time limit, a donor heart cannot be transplanted into a recipient who is located more than 500 miles (800 km) from the harvest. In the United States, this means that a critically-ill patient in Chicago will be denied access to a matching donor heart from New York City. If the geographic range of donors could be extended, thousands of lives would be saved each year.

While several state-of-the-art preservation methods are available to keep organs viable within a hospital, transport preservation typically involves simple hypothermic (less than 10° C.) storage. Contemporary transport storage (i.e. "picnic cooler" storage) typically involves bagging the organ in cold preservation solution and placing the bagged organ in a portable cooler along with ice for the journey. There are no additional nutrients or oxygen provided to the organ. For the most part, the hope is that the preservation solution will reduce swelling and keep the tissues moist, while the cold reduces tissue damage due to hypoxia.

This method of transport has several known shortcomings, however. First, the temperature is not stabilized. Because the temperature of the organ is determined by the rate of melting and the thermal losses of the cooler, an organ will experience a wide range of temperatures during transport. For example, the temperatures can range from nearly 0° C., where the organ risks freezing damage, to 10-15° C., or greater, where the organ experiences greater tissue damage due to hypoxia.

Second, the organ does not receive sufficient oxygen and nutrients. Even though the metabolic rate is greatly slowed by the low temperatures, the tissues still require oxygen and nutrients to be able to function normally once the tissue is warmed. While some nutrients are provided by the preservation fluid surrounding the organ, the nutrients are not readily absorbed by the exterior of the organ due to the presence of a protective covering, e.g., the renal capsule.

Third, there is little protection against mechanical shock. An organ sealed in bag and then placed in a cooler with ice is subject to bruising and abrasion as the organ contacts ice chunks or the sides of the cooler. Mechanical damage can be especially problematic when the organ is airlifted and the aircraft experiences turbulence.

Fourth, there is no way to monitor the conditions during transport. Monitoring temperature and oxygen consumption, for example, would give an indication of the condition of the organ. Such information could be used by a transport team to correct conditions, e.g., add more ice, or to indicate that the organ may not be suitable for transplant.

Improved transport and storage for organs would increase the pool of available organs while improving outcomes for recipients.

SUMMARY

The invention provides an improved system for transporting biological samples, e.g. tissues, such as donor organs. This improved system will greatly expand the window of time for organ transportation and will, consequently, make many more organs available for donation. Additionally, the samples will be healthier upon arrival, as compared to state-of-the-art transport methods.

The disclosed system for hypothermic transport overcomes the shortcomings of the prior art by providing a sterile, temperature-stabilized environment for the samples while providing the ability to monitor the temperature of the samples during transport. Additionally, because the samples are suspended in an oxygenated preservation fluid, the delivered samples avoid mechanical damage, remain oxygenated, and are delivered healthier than samples that have been merely sealed in a plastic bag.

In some cases in which the sample is a tissue, the preservation solution is circulated through the tissue using the tissue's cardiovascular system. In this case, a pulsed flow is used to imitate the natural environment of the tissue. Such conditions improve absorption of nutrients and oxygen as compared to static storage. Additionally, because compressed oxygen is used to propel the pulsed circulation, the preservation fluid is reoxygenated during transport, replacing the oxygen that has been consumed by the tissue and displacing waste gases (i.e., $CO_2$). In some instances, a suite of sensors measures temperature, oxygen content, and pressure of the circulating fluids to assure that the tissue experiences a favorable environment during the entire transport.

In one version of the invention, the system includes a first transport container configured to suspend a biological sample (e.g., tissue or an organ) in an oxygenated preservation fluid. The first transport container includes a temperature sensor and a temperature display, thereby allowing a user to continually monitor the temperature of the tissue. The system also includes a second transport container having an insulated cavity for receiving the first transport container, and having recesses for receiving cooling media.

In another version of the invention, the system includes a first transport container that has a pumping chamber to circulate a fluid inside the first transport container. The first transport container includes a temperature sensor and a temperature display, thereby allowing a user to continually monitor the temperature of the tissue. The system also includes a second transport container having an insulated cavity for receiving the first transport container and having recesses for receiving cooling media.

For both versions above, the cooling media will typically be one or more eutectic cooling blocks. The cooling blocks provide regulated cooling in the range of 4-8° C. for twelve or more hours. The system may additionally include an oxygen source, for example a compressed gas cylinder, to provide oxygen to the biological sample. In some versions, the system will have sensors and displays to monitor conditions in addition to temperature, for example oxygen or pressure. In some versions, the sensors that monitor, for example, the temperature of the sample, will be coupled to a wireless transmitter that communicates with a second display located on the exterior of the second transport container. Accordingly, a user can monitor the temperature of the biological sample within the first transport container while the first transport container is securely stored within the second transport container.

A further advantage of the disclosed system is that the first transport container includes both a temperature sensor and a temperature display, allowing a user to monitor the temperature within the first transport container independently of the second transport container. This feature allows a user to monitor the temperature of the sample or the preservation fluid immediately after the sample is placed in the first transport container, but prior to being placed in the second transport container, as well as after the first transport container is removed from the second transport container, for example, in the operating room prior to implantation of the tissue. Because the first transport container includes both a temperature sensor and a temperature display it is also possible to observe the temperature of the sample during a warming period without having to open the first transport container.

The invention also includes methods for transporting biological samples (e.g., tissue or an organ). The method includes providing a hypothermic transport system of the invention, suspending the biological sample in preservation fluid within the first transport container, and maintaining the temperature of the preservation fluid between 2 and 8° C. for at least 60 minutes. Hypothermic transport systems of the invention, suitable for use with the method include a first transport container configured to suspend the sample in a preservation fluid, and having a temperature sensor and a temperature display, and a second transport container comprising an insulated cavity for receiving the first transport container and also having recesses for receiving cooling media. The preservation fluid is typically maintained at a pressure greater than atmospheric pressure, and is typically oxygenated, for example by an oxygen source such as a cylinder of compressed gas. In some instances, the preservation fluid is circulated around a tissue suspended in the first transport container. In other instances the preservation fluid is perfused through an organ suspended in the first transport container. In some instances, an organ is perfused with preservation solution by using oscillating pressures, thereby simulating the systolic and diastolic pressures experienced by circulatory system of the organ while in the body. In another instance, a body fluid may be transported by suspending a third container (e.g., a blood bag) within the first transport container.

DETAILED DESCRIPTION

The disclosed systems for hypothermic transport of samples provides a sterile, temperature-stabilized environment for transporting samples while providing an ability to monitor the temperature of the samples during transport. Because of these improvements, users of the invention can reliably transport samples over much greater distances, thereby substantially increasing the pool of available tissue donations. Additionally, because the tissues are in better condition upon delivery, the long-term prognosis for the recipient is improved.

Hypothermic transport systems of the invention comprise a first transport container and a second transport container. The first transport container will receive the tissue for transport, and keep it suspended or otherwise supported in a surrounding pool of preservation solution. The first transport container may comprise a number of configurations suitable to transport tissues hypothermicly, provided that the first transport container includes a temperature sensor and a display. For example, the first transport container could be of a type disclosed in U.S. patent application Ser. No. 13/420,962, filed Mar. 15, 2012, and incorporated by reference herein in its entirety.

In some embodiments, the first transport container will include a pumping mechanism to circulate the preservation solution or perfuse an organ with the preservation solution. A first transport container comprising a pumping chamber will be referred to as "pulsatile." While the pumping is pulsating in preferred embodiments, the pumping is not intended to be limited to pulsating pumping, that is, the pumping may be continuous. In other embodiments, the first transport container will not circulate or perfuse the preservation solution. A non-pumping first transport container will be referred to as "static."

Figure 1:
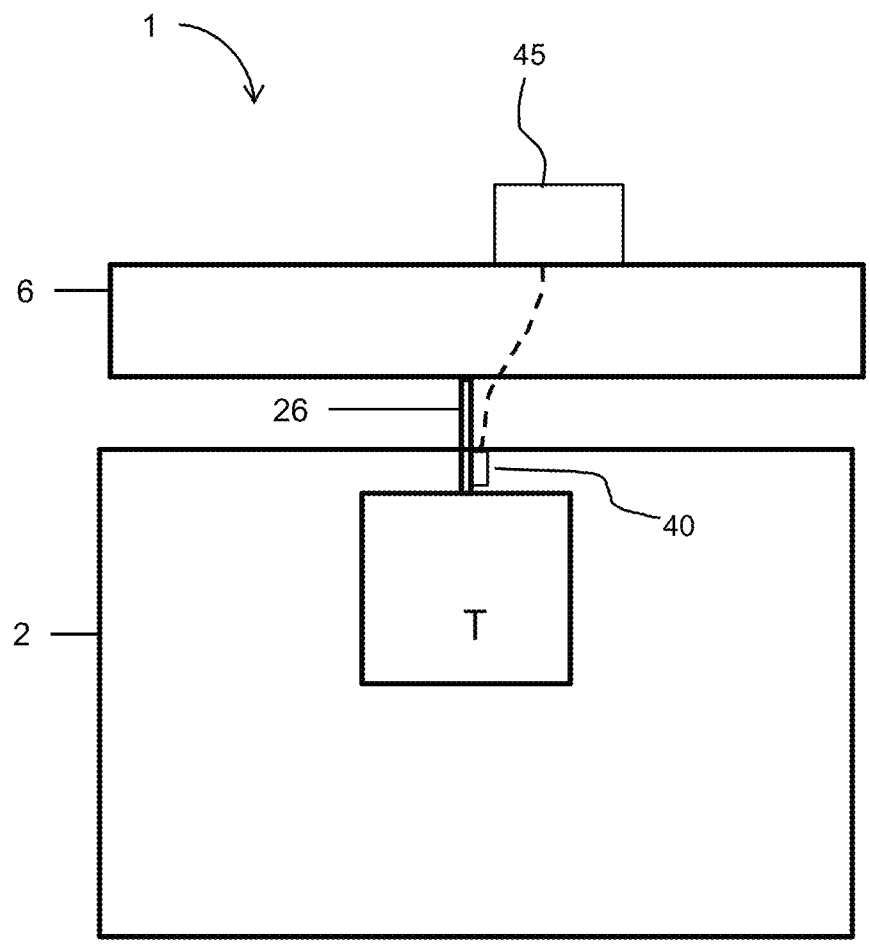
FIG. 1 shows an embodiment of a first transport container suitable for use as part of a hypothermic transport system of the invention. The container comprises a tissue storage vessel and a lid.

A general schematic of a static first transport container 1 is shown in FIG. 1. The static first transport container 1 includes a storage vessel 2 and a lid without a pumping chamber 6. The lid without a pumping chamber 6 is coupled to an adapter 26 which can be used to suspend a tissue T to be transported. The adapter 26 can be coupled to the tissue T in any suitable manner. It should be noted that the tissue T shown in the figures is for illustrative purposes only. That is, the invention is intended for the transport of biological samples, generally, which may include tissues, organs, body fluids, and combinations thereof.

The static first transport container 1 also includes a temperature sensor 40 which is coupled to a temperature display 45 disposed on the exterior of the static first transport container 1. While the temperature display 45 is shown disposed on the exterior of the lid 6, it could also be disposed on the exterior of the storage vessel 2. Typically, the tissue T will be affixed to the adapter 26, coupled to the lid 6, and then the lid 6 and the tissue T will be immersed into preservation solution held by storage vessel 2. The lid 6 will then be sealed to the storage vessel 2 using a coupling or fastener (not shown). In some embodiments, the lid 6 or the storage vessel will have entrance and exit ports (not shown) to allow a user to purge the sealed static first transport container 1 by forcing additional preservation fluid into the sealed container.

The storage vessel 2, lid without a pumping chamber 6, and adapter are constructed of durable materials that are suitable for use with a medical device. Additionally, the transport container should be constructed of materials that conduct heat so that the sample within the container is adequately cooled by the cooling media (see discussion below). For example, the lid 6 and storage vessel 2 may be constructed of stainless steel. In other embodiments, because it is beneficial to be able to view the contents directly, the lid 6 and storage vessel may be constructed of medical acrylic (e.g., PMMA) or another clear medical polymer.

It is additionally beneficial for the storage vessel 2, lid without a pumping chamber 6, and adapter to be sterilizable, i.e., made of a material that can be sterilized by steam (autoclave) or with UV irradiation, or another form of sterilization. Sterilization will prevent tissues from becoming infected with viruses, bacteria, etc., during transport. In a typical embodiment the first transport container will be delivered in a sterile condition and sealed in sterile packaging. In some embodiments, the first transport container will be sterilized after use prior to reuse, for example a hospital. In other embodiments, the first transport container will be disposable.

The temperature sensor 40 may be any temperature reading device that can be sterilized and maintained in cold fluidic environment, i.e., the environment within the static first transport container 1 during transport of tissue T. The temperature sensor 40 may be a thermocouple, thermistor, infrared thermometer, or liquid crystal thermometer. When the static first transport container 1 is sealed, temperature sensor 40 is typically disposed in contact with the cold preservation solution and in proximity to the tissue T such that a temperature of the tissue T can be ascertained during transport. Temperature display 45 may be coupled to the temperature sensor 40 using any suitable method, for example a wire, cable, connector, or wirelessly using available wireless protocols. In some embodiments, the temperature sensor 40 may be attached to the adapter 26. In some embodiment, the temperature sensor 40 is incorporated into the adapter 26 to improve the mechanical stability of the temperature sensor 40.

The temperature display 45 can be any display suitable for displaying a temperature measured by the temperature sensor 40, or otherwise providing information about the temperature within the static first transport container 1. For example, the temperature display can be a light emitting diode (LED) display or liquid crystal display (LCD) showing digits corresponding to a measured temperature. The display may alternatively comprise one or more indicator lights, for example an LED which turns on or off or flashes to indicated whether the temperature measured by the temperature sensor 40 is within an acceptable range, e.g., 2-8° C., e.g., 4-6° C., e.g., about 4° C. The temperature sensor 40 may also be connected to a processor (not shown) which will compare the measured temperature to a threshold or range and create an alert signal when the temperature exceeds the threshold or range. The alert may comprise an audible tone, or may signal to a networked device, e.g., a computer, cell phone, or pager that the temperature within the container exceeds the desired threshold or range.

The adapter 26 may be of a variety of structures suitable to suspend the tissue T in the preservation solution while minimizing the potential for mechanical damage, e.g., bruising or abrasion. In some embodiments, the adapter 26 is configured to be sutured to the tissue T. In another example, the adapter 26 is coupleable to the tissue T via an intervening structure, such as silastic or other tubing. In some embodiments, at least a portion of the adapter 26, or the intervening structure, is configured to be inserted into the tissue T. In some embodiments, the adapter 26 is configured to support the tissue T when the tissue T is coupled to the adapter. For example, in some embodiments, the adapter 26 includes a retention mechanism configured to be disposed about at least a portion of the tissue T and to help retain the tissue T with respect to the adapter. The retention mechanism can be, for example, a net, a cage, a sling, or the like.

Figure 2:
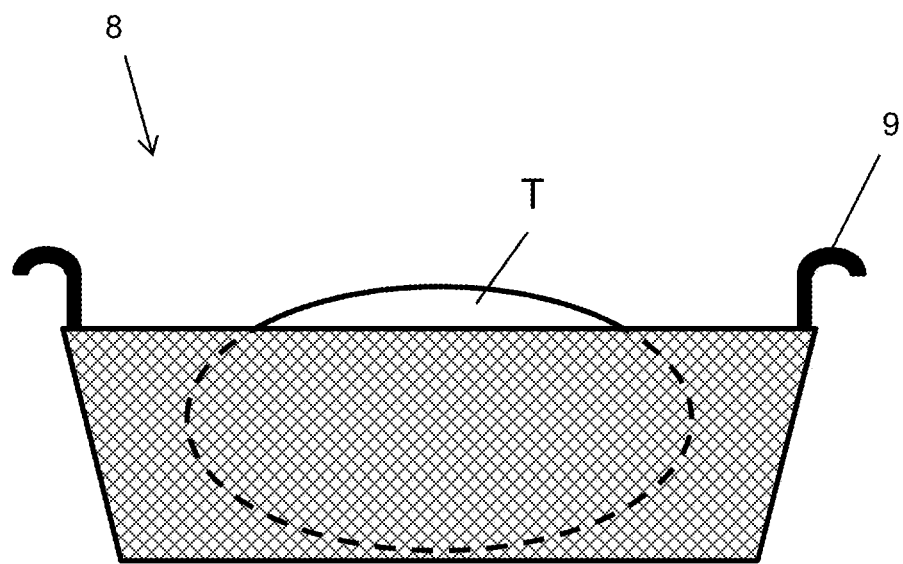
FIG. 2 shows a basket insert for suspending a biological sample within a first transport container.

In some embodiments, a first transport container may additionally include a basket 8 or other support mechanism configured to support the tissue T when the tissue T is coupled to the adapter 26 or otherwise suspended in the first transport container. The support mechanism may be part of an insert which fits within the first transport container, such as shown in FIG. 2. The basket 8 may include connectors 9 which may be flexible or hinged to allow the basket 8 to move in response to mechanical shock, thereby reducing the possibility of damage to tissue T. In other embodiments, the basket 8 may be coupled to the lid 6 so that it is easily immersed in and retracted from the preservation fluid held in the storage vessel 2.

Figure 3:
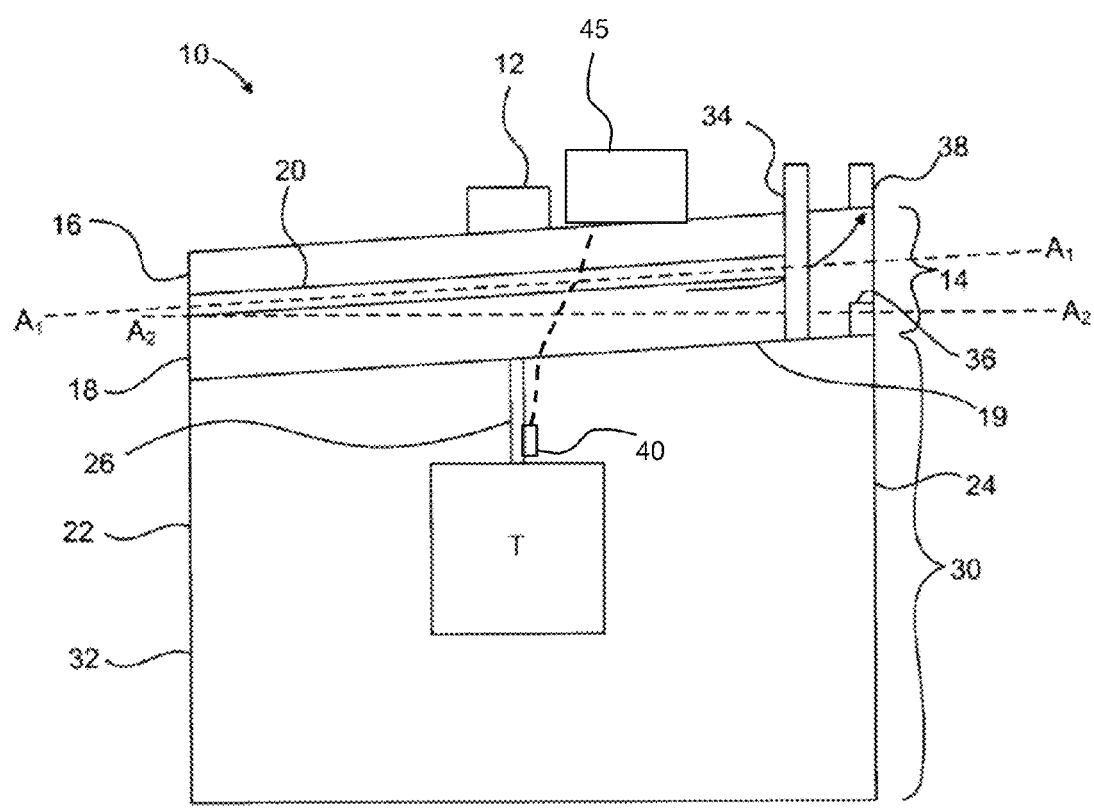
FIG. 3 shows an embodiment of first transport container suitable for use as part of a hypothermic transport system of the invention. In contrast to FIG. 1, the lid of the transport container of FIG. 3 comprises a pumping chamber for circulating or perfusing a preservation solution.

In some instances, the first transport container will be equipped to pump or circulate the preservation fluid. A pulsatile first transport container 10 is shown in FIG. 3. The pulsatile first transport container 10 is configured to oxygenate a preservation fluid received in a pumping chamber 14 of the apparatus. The pulsatile first transport container 10 includes a valve 12 configured to permit a fluid (e.g., oxygen) to be introduced into a first portion 16 of the pumping chamber 14. A membrane 20 is disposed between the first portion 16 of the pumping chamber 14 and a second portion 18 of the pumping chamber. The membrane 20 is configured to permit the flow of a gas between the first portion 16 of the pumping chamber 14 and the second portion 18 of the pumping chamber through the membrane. The membrane 20 is configured to substantially prevent the flow of a liquid between the second portion 18 of the pumping chamber 14 and the first portion 16 of the pumping chamber through the membrane. In this manner, the membrane can be characterized as being semi-permeable.

The membrane 20 is disposed within the pumping chamber 14 along an axis A1 that is transverse to a horizontal axis A2. Said another way, the membrane 20 is inclined, for example, from a first side 22 to a second side 24 of the apparatus 10. As such, a rising fluid in the second portion 18 of the pumping chamber 14 will be directed by the inclined membrane 20 toward a port 38 disposed at the highest portion of the pumping chamber 14. The port 38 is configured to permit the fluid to flow from the pumping chamber 14 into the atmosphere external to the apparatus 10. In some embodiments, the port 38 is configured for unidirectional flow, and thus is configured to prevent a fluid from being introduced into the pumping chamber 14 via the port (e.g., from a source external to the pulsatile first transport container 10). In some embodiments, the port 38 includes a luer lock.

The second portion 18 of the pumping chamber 14 is configured to receive a fluid. In some embodiments, for example, the second portion 18 of the pumping chamber 14 is configured to receive a preservation fluid. The second portion 18 of the pumping chamber 14 is in fluid communication with the adapter 26. In pulsatile first transport container 10, the adapter 26 is configured to permit movement of the fluid from the pumping chamber 14 to a tissue T. In some embodiments, the pumping chamber 14 defines an aperture configured to be in fluidic communication with a lumen (not shown) of the adapter 26. The adapter 26 is configured to be coupled to the tissue T. The adapter 26 can be coupled to the tissue T in any suitable manner. For example, in some embodiments, the adapter 26 is configured to be sutured to the tissue T. In another example, the adapter 26 is coupleable to the tissue T via an intervening structure, such as silastic or other tubing. In some embodiments, at least a portion of the adapter 26, or the intervening structure, is configured to be inserted into the tissue T. For example, in some embodiments, the lumen of the adapter 26 (or a lumen of the intervening structure) is configured to be fluidically coupled to a vessel of the tissue T. In other embodiments, the tissue T may be suspended in a basket 8 and not connected to the adapter 26. In these embodiments, the pumping chamber serves to circulate the preservation fluid, however the tissue T is not perfused. In some embodiments, the adapter 26 is configured to support the tissue T when the tissue T is coupled to the adapter. For example, in some embodiments, the adapter 26 includes a retention mechanism (not shown) configured to be disposed about at least a portion of the tissue T and to help retain the tissue T with respect to the adapter. The retention mechanism can be, for example, a net, a cage, a sling, or the like.

An organ chamber 30 is configured to receive the tissue T and a fluid. In some embodiments, the pulsatile first transport container 10 includes a port 34 that is extended through the pulsatile first transport container 10 (e.g., through the pumping chamber 14) to the organ chamber 30. The port 34 is configured to permit fluid (e.g., preservation fluid) to be introduced to the organ chamber 30. In this manner, fluid can be introduced into the organ chamber 30 as desired by an operator of the apparatus. For example, in some embodiments, a desired amount of preservation fluid is introduced into the organ chamber 30 via the port 34, such as before disposing the tissue T in the organ chamber 30 and/or while the tissue T is received in the organ chamber. In some embodiments, the port 34 is a unidirectional port, and thus is configured to prevent the flow of fluid from the organ chamber 30 to an area external to the organ chamber through the port. In some embodiments, the port 34 includes a luer lock. The organ chamber 30 may be of any suitable volume necessary for receiving the tissue T and a requisite amount of fluid for maintaining viability of the tissue T. In one embodiment, for example, the volume of the organ chamber 30 is approximately 2 liters.

The organ chamber 30 is formed by a canister 32 and a bottom portion 19 of the pumping chamber 14. In a similar manner as described above with respect to the membrane 20, an upper portion of the organ chamber (defined by the bottom portion 19 of the pumping chamber 14) can be inclined from the first side 22 towards the second side 24 of the apparatus. In this manner, a rising fluid in the organ chamber 30 will be directed by the inclined upper portion of the organ chamber towards a valve 36 disposed at a highest portion of the organ chamber. The valve 36 is configured to permit a fluid to flow from the organ chamber 30 to the pumping chamber 14. The valve 36 is configured to prevent flow of a fluid from the pumping chamber 14 to the organ chamber. The valve 36 can be any suitable valve for permitting unidirectional flow of the fluid, including, for example, a ball check valve.

The canister 32 can be constructed of any suitable material. In some embodiments, the canister 32 is constructed of a material that permits an operator of the pulsatile first transport container 10 to view at least one of the tissue T or the preservation fluid received in the organ chamber 30. For example, in some embodiments, the canister 32 is substantially transparent. In another example, in some embodiments, the canister 32 is substantially translucent. The organ chamber 30 can be of any suitable shape and/or size. For example, in some embodiments, the organ chamber 30 can have a perimeter that is substantially oblong, oval, round, square, rectangular, cylindrical, or another suitable shape.

Like the static first transport container 1, a pulsatile first transport container 10 also includes a temperature sensor 40 which is coupled to a temperature display 45 disposed on the exterior of the pulsatile first transport container 10. While the temperature display 45 is shown disposed on the pumping chamber 14, it could also be disposed on the canister 32. Typically, the tissue T will be affixed to the adapter 26, coupled to the pumping chamber 14, and then the pumping chamber 14 and the tissue T will be immersed into preservation solution held by organ chamber 30.

The temperature sensor 40 may be any temperature reading device that can be sterilized and maintained in cold fluidic environment, i.e., the environment within the static first transport container 1 during transport of tissue T. The temperature sensor 40 may be a thermocouple, thermistor, infrared thermometer, or liquid crystal thermometer. When the static first transport container 1 is sealed, temperature sensor 40 is typically disposed in contact with the cold preservation solution and in proximity to the tissue T such that a temperature of the tissue T can be ascertained during transport. Temperature display 45 may be coupled to the temperature sensor 40 using any suitable method, for example a wire, cable, connector, or wirelessly using available wireless protocols. In some embodiments, the temperature sensor 40 may be attached to the adapter 26. In some embodiment, the temperature sensor 40 is incorporated into the adapter 26 to improve the mechanical stability of the temperature sensor 40.

The temperature display 45 can be any display suitable for displaying a temperature measured by the temperature sensor 40, or otherwise providing information about the temperature within the pulsatile first transport container 10. For example, the temperature display can be a light emitting diode (LED) display or liquid crystal display (LCD) showing digits corresponding to a measured temperature. The display may alternatively comprise one or more indicator lights, for example an LED which turns on or off or flashes to indicate whether the temperature of measured by the temperature sensor 40 is within an acceptable range, e.g., 2-8° C., e.g., 4-6° C., e.g., about 4° C. The temperature sensor 40 may also be connected to a processor (not shown) which will compare the measured temperature to a threshold or range and create an alert signal when the temperature exceeds the threshold or range. The alert may comprise an audible tone, or may signal to a networked device, e.g., a computer, cell phone, or pager that the temperature within the container exceeds the desired threshold or range.

In use, the tissue T is coupled to the adapter 26. The pumping chamber 14 is coupled to the canister 32 such that the tissue T is received in the organ chamber 30. In some embodiments, the pumping chamber 14 and the canister 32 are coupled such that the organ chamber 30 is hermetically sealed. A desired amount of preservation fluid is introduced into the organ chamber 30 via the port 34. The organ chamber 30 can be filled with the preservation fluid such that the preservation fluid volume rises to the highest portion of the organ chamber. The organ chamber 30 can be filled with an additional amount of preservation fluid such that the preservation fluid flows from the organ chamber 30 through the valve 36 into the second portion 18 of the pumping chamber 14. The organ chamber 30 can continue to be filled with additional preservation fluid until all atmospheric gas that initially filled the second portion 18 of the pumping chamber 14 rises along the inclined membrane 20 and escapes through the port 38. Because the gas will be expelled from the pumping chamber 14 via the port 38 before any excess preservation fluid is expelled (due to gas being lighter, and thus more easily expelled, than liquid), an operator of the pulsatile first transport container 10 can determine that substantially all excess gas has been expelled from the pumping chamber when excess preservation fluid is released via the port. As such, the pulsatile first transport container 10 can be characterized as self-purging.

Oxygen (or another suitable fluid, e.g., dry air) is introduced into the first portion 16 of the pumping chamber 14 via the valve 12. A positive pressure generated by the introduction of oxygen into the pumping chamber 14 causes the oxygen to be diffused through the semi-permeable membrane 20 into the second portion 18 of the pumping chamber. Because oxygen is a gas, the oxygen expands to substantially fill the first portion 16 of the pumping chamber 14. As such, substantially the entire surface area of the membrane 20 between the first portion 16 and the second portion 18 of the pumping chamber 14 is used to diffuse the oxygen. The oxygen is diffused through the membrane 20 into the preservation fluid received in the second portion 18 of the pumping chamber 14, thereby oxygenating the preservation fluid.

In the presence of the positive pressure, the oxygenated preservation fluid is moved from the second portion 18 of the pumping chamber 14 into the tissue T via the adapter 26. For example, the positive pressure can cause the preservation fluid to move from the pumping chamber 14 through the lumen of the adapter 26 into the vessel of the tissue T. The positive pressure is also configured to help move the preservation fluid through the tissue T such that the tissue T is perfused with oxygenated preservation fluid.

After the preservation fluid is perfused through the tissue T, the preservation fluid is received in the organ chamber 30. In this manner, the preservation fluid that has been perfused through the tissue T is combined with preservation fluid previously disposed in the organ chamber 30. In some embodiments, the volume of preservation fluid received from the tissue T following perfusion combined with the volume of preservation fluid previously disposed in the organ chamber 30 exceeds a volume (e.g., a maximum fluid capacity) of the organ chamber 30. A portion of the organ chamber 30 is flexible and expands to accept this excess volume. The valve 12 can then allow oxygen to vent from the first portion 16 of the pumping chamber 14, thus, reducing the pressure in the pumping chamber 14. As the pressure in the pumping chamber 14 drops, the flexible portion of the organ chamber 30 relaxes, and the excess preservation fluid is moved through the valve 36 into the pumping chamber 14. The cycle of oxygenating preservation fluid and perfusing the tissue T with the oxygenated reservation fluid can be repeated as desired.

Figure 4:
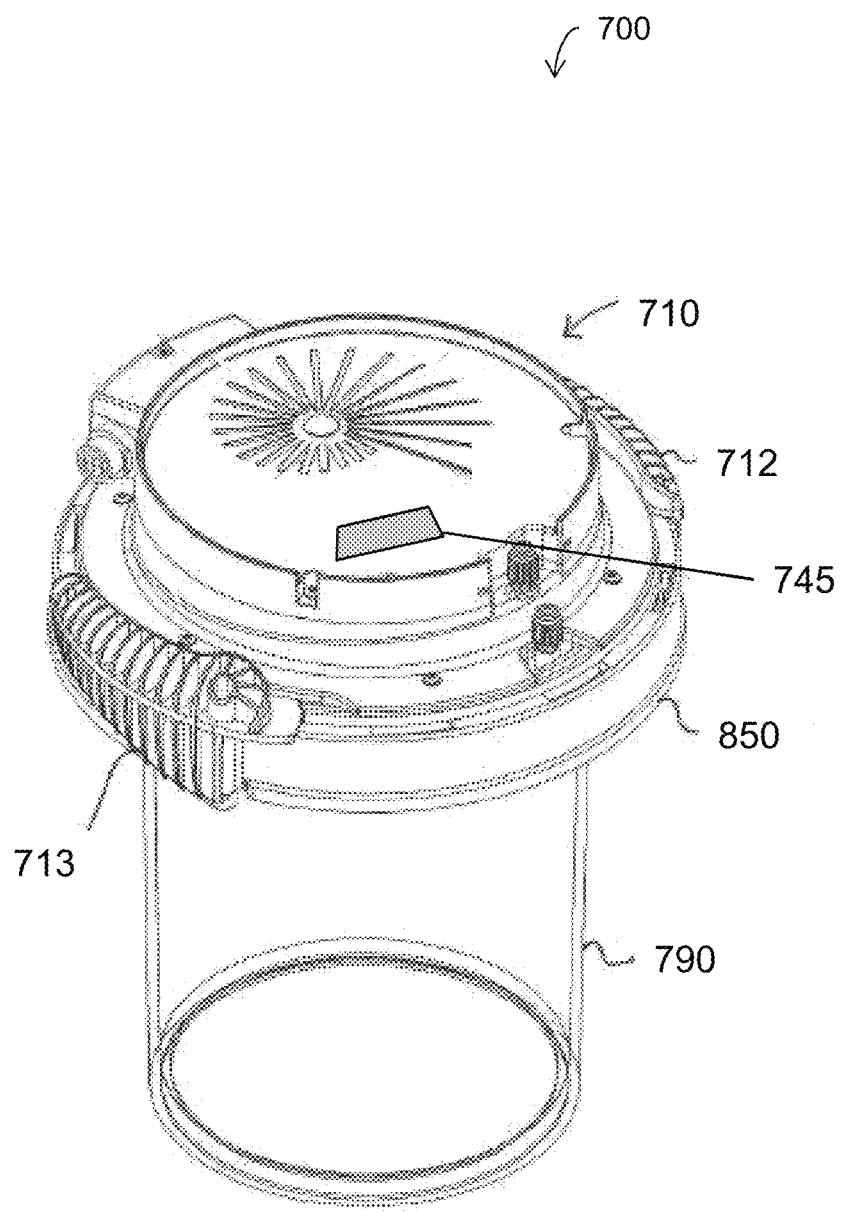
FIG. 4 is a perspective view of a first transport container suitable for use with a hypothermic transport system of the invention.

A perspective view of a first transport container suitable for use as a portion of a system of the invention is shown in FIG. 4. First transport container 700 comprises a lid assembly 710 having a temperature display 745, a canister 790, and a coupling mechanism 850 between the lid 710 and the canister 790. The first transport container 700 may be hermetically sealed by actuating clamps 712 and 713, sealing the coupling mechanism 850, once the tissue and preservation fluid has been placed within. As shown in FIG. 4, the canister may be substantially transparent, allowing a user to view the condition of the tissue during transport.

Figure 5:
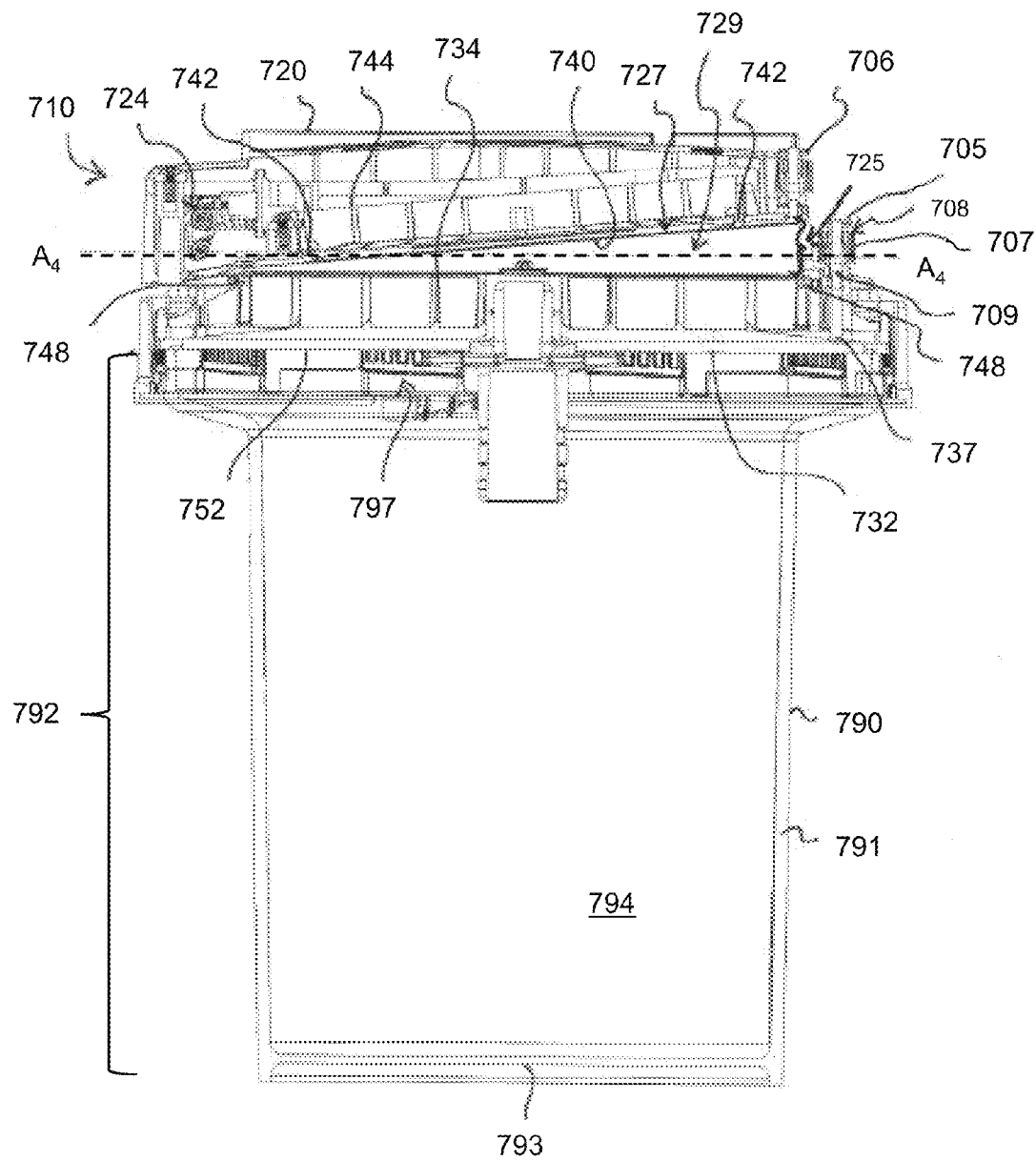
FIG. 5 is a cross-sectional view of a first transport container suitable for use with a hypothermic transport system of the invention. The lid of the container comprises a pumping chamber for circulating or perfusing a preservation solution.

A cut-away view of first transport container capable of perfusing an organ with preservation fluid is shown in FIG. 5. It includes a lid assembly 710, a canister 790, and a coupling mechanism 850. While it is not shown in this view, the first transport container additionally comprises a temperature sensor and a display. The lid assembly 710 defines a chamber 724 configured to receive components of a pneumatic system (not shown) and necessary control electronics. In some embodiments, the chamber 724 is formed by a lid 720 of the lid assembly 710. In some embodiments, the chamber 724 can be formed between a lower portion 723 of the lid 720 and an upper portion 722 of the lid. In some embodiments the canister 790 is configured to receive a basket 8, such as shown in FIG. 3.

The lid assembly 710 defines a pumping chamber 725 configured to receive oxygen to facilitate diffusion of the oxygen into a preservation fluid (not shown) and to facilitate movement of the oxygenated preservation fluid throughout the storage container. A top of the pumping chamber 725 is formed by a lower portion 728 of a membrane frame 744 of the lid assembly 710. A bottom of the pumping chamber 725 is formed by an upper surface 734 of a base 732 of the lid assembly 710.

The lid assembly 710 may include a first gasket 742, a membrane 740, and the membrane frame 744. The membrane 740 is disposed within the pumping chamber 725 and divides the pumping chamber 725 into a first portion 727 and a second portion 729 different than the first portion. The first gasket 742 is disposed between the membrane 740 and the membrane frame 744 such that the first gasket is engaged with an upper surface 741 of the membrane 740 and a lower, perimeter portion of the membrane frame 744. The first gasket 742 is configured to seal a perimeter of the first portion 727 of the pumping chamber 725 twined between the lower portion 728 of the membrane frame 744 and the upper surface 741 of the membrane 740. In other words, the first gasket 742 is configured to substantially prevent lateral escape of oxygen from the first portion 727 of the pumping chamber 725 to a different portion of the pumping chamber. In the embodiment illustrated in FIG. 5, the first gasket 742 has a perimeter substantially similar in shape to a perimeter defined by the membrane 740 (e.g., when the membrane is disposed on the membrane frame 744). In other embodiments, however, a first gasket can have another suitable shape for sealing a first portion of a pumping chamber configured to receive oxygen from a pneumatic system.

The first gasket 742 can be constructed of any suitable material. In some embodiments, for example, the first gasket 742 is constructed of silicone, an elastomer, or the like. The first gasket 742 can have any suitable thickness. For example, in some embodiments, the first gasket 742 has a thickness within a range of about 0.1 inches to about 0.15 inches. More specifically, in some embodiments, the first gasket 742 has a thickness of about 0.139 inches. The first gasket 742 can have any suitable level of compression configured to maintain the seal about the first portion 727 of the pumping chamber 725 when the components of the lid assembly 710 are assembled. For example, in some embodiments, the first gasket 742 is configured to be compressed by about 20 percent.

The membrane 740 is configured to permit diffusion of gas (e.g., oxygen) from the first portion 727 of the pumping chamber 725 through the membrane to the second portion 729 of the pumping chamber, and vice versa. The membrane 740 is configured to substantially prevent a liquid (e.g., the preservation fluid) from passing through the membrane. In this manner, the membrane 740 can be characterized as being semi-permeable. The membrane frame 744 is configured to support the membrane 740 (e.g., during the oxygenation of the preservation fluid and perfusion of the tissue). The membrane frame 744 can have a substantially round or circular shaped perimeter. The membrane frame 744 includes a first port 749A and a second port 749B. The first port 749A is configured to convey fluid between the first portion 727 of the pumping chamber and the pneumatic system (not shown). For example, the first port 749A can be configured to convey oxygen from the pneumatic system to the first portion 727 of the pumping chamber 725. The second port 749B is configured to permit a pressure sensor line (not shown) to be disposed therethrough. The pressure sensor line can be, for example, polyurethane tubing. The ports 749A, 749B can be disposed at any suitable location on the membrane frame 744, including, for example, towards a center of the membrane frame 744. Although the ports 749A, 749B are shown in close proximity, in other embodiments, the ports 749A, 749B can be differently spaced (e.g., closer together or further apart).

At least a portion of the membrane 740 is disposed (e.g., wrapped) about at least a portion of the membrane frame 744. In some embodiments, the membrane 740 is stretched when it is disposed on the membrane frame 744. The membrane 740 is disposed about a lower edge or rim of the membrane frame 744 and over at least a portion of an outer perimeter of the membrane frame 744 such that the membrane 740 is engaged with a series of protrusions (e.g., protrusion 745) configured to help retain the membrane with respect to the membrane frame. The membrane frame 744 is configured to be received in a recess 747 defined by the lid 720. As such, the membrane 740 is engaged between the membrane frame 744 and the lid 720, which facilitates retention of the membrane with respect to the membrane frame. In some embodiments, the first gasket 742 also helps to maintain the membrane 740 with respect to the membrane frame 744 because the first gasket is compressed against the membrane between the membrane frame 744 and the lid 720.

As illustrated in FIG. 5, the membrane 740 is disposed within the pumping chamber 725 at an angle with respect to a horizontal axis A4. In this manner, the membrane 740 is configured to facilitate movement of fluid towards a purge port 706 in fluid communication with the pumping chamber 725, as described in more detail herein. The angle of incline of the membrane 740 can be of any suitable value to allow fluid (e.g., gas bubbles, excess liquid) to flow towards the purge port 706 and exit the pumping chamber 725. In some embodiments, the angle of incline is approximately in the range of 1°-10°, in the range of 2°-6°, in the range of 2.5°-5°, in the range of 4°-5° or any angle of incline in the range of 1°-10° (e.g., approximately 1°, 2°, 3°, 4°, 5°, 6°, 7°, 8°, 9°, 10°). More specifically, in some embodiments, the angle of incline is approximately 5°.

The membrane 740 can be of any suitable size and/or thickness, including, for example, a size and/or thickness described with respect to another membrane herein (e.g., membrane 140). The membrane 740 can be constructed of any suitable material. For example, in some embodiments, the membrane is constructed of silicone, plastic, or another suitable material. In some embodiments, the membrane is flexible. The membrane 740 can be substantially seamless. In this manner, the membrane 740 is configured to be more resistant to being torn or otherwise damaged in the presence of a flexural stress caused by a change in pressure in the pumping chamber due to the inflow and/or release of oxygen or another gas.

The lid 720 includes the purge port 706 disposed at the highest portion of the pumping chamber 725 (e.g., at the highest portion or point of the second portion 729 of the pumping chamber 725). The purge port 706 is configured to permit movement of fluid from the pumping chamber 725 to an area external to the first transport container 700. The purge port 706 can be similar in many respects to a purge port described herein (e.g., port 78, purge ports 106, 306).

Optionally, a desired amount of preservation fluid can be disposed within the compartment 794 of the canister 790 prior to disposing the lid assembly 710 on the canister. For example, in some embodiments, a preservation fluid line (not shown) is connected to the storage chamber 792 and the device is flushed with preservation fluid, thereby checking for leaks and partially filling the canister 790 with preservation fluid. Optionally, when the canister 790 is substantially filled, the preservation fluid line can be disconnected. The lid assembly 710 is disposed on the canister 790 such that the body fluids, held by holder 726, are immersed in the storage chamber 792. The lid assembly 710 is coupled to the canister 790. Optionally, the lid assembly 710 and the canister 790 are coupled via the retainer ring 850. Optionally, a desired amount of preservation fluid is delivered to the storage chamber 792 via the fill port 708. In some embodiments, a volume of preservation fluid greater than a volume of the storage chamber 792 is delivered to the storage chamber such that the preservation fluid will move through the valves 738A, 738B into the second portion 729 of the pumping chamber 725.

In the embodiment shown in FIG. 5, oxygen may be introduced into the first portion 727 of the pumping chamber 725 via a pneumatic system. The pneumatic system is configured to generate a positive pressure by the introduction of oxygen into the first portion 727 of the pumping chamber 725. The positive pressure helps to facilitate diffusion of the oxygen through the membrane 740. The oxygen is diffused through the membrane 740 into the preservation solution disposed in the second portion 729 of the pumping chamber 725, thereby oxygenating the preservation solution. Because the oxygen will expand to fill the first portion 727 of the pumping chamber 725, substantially all of an upper surface 741 of the membrane 740 which faces the first portion of the pumping chamber can be used to diffuse the oxygen from the first portion into the second portion 729 of the pumping chamber.

As the tissue consumes oxygen, the tissue will release carbon dioxide into the preservation fluid. Such carbon dioxide can be diffused from the second portion 729 of the pumping chamber 725 into the first portion 727 of the pumping chamber 725. Carbon dioxide within the first portion 727 of the pumping chamber is vented via a control line (not shown) to a valve (not shown), and from the valve through a vent line (not shown) to the atmosphere external to the first transport container. The positive pressure also causes the membrane 740 to flex, which transfers the positive pressure in the form of a pulse wave into the oxygenated preservation fluid. The pulse wave generated by the pumping chamber is configured to facilitate circulation of the oxygenated preservation fluid from the second portion 729 of the pumping chamber 725 into storage chamber 792 thereby contacting the tissue or being perfused through the tissue.

At least a portion of the preservation fluid contacting the tissue is received in the storage chamber 792. In some embodiments, the pulse wave is configured to flow through the preservation solution disposed in the storage chamber 792 towards the floor 793 of the canister 790. The floor 793 of the canister 790 is configured to flex when engaged by the pulse wave. The floor 793 of the canister 790 is configured to return the pulse wave through the preservation fluid towards the top of the storage chamber 792 as the floor 793 of the canister 790 is returned towards its original non-flexed position. In some embodiments, the returned pulse wave is configured to generate a sufficient pressure to open the valves 738A, 738B disposed at the highest positions in the storage chamber 792. In this manner, the returned pulse wave helps to move the valves 738A, 738B to their respective open configurations such that excess fluid (e.g., carbon dioxide released from the body fluid and/or the preservation fluid) can move through the valves from the storage chamber 792 to the pumping chamber 725. The foregoing cycle can be repeated as desired, including in any manner described above with respect to other apparatus described herein.

Figure 6:
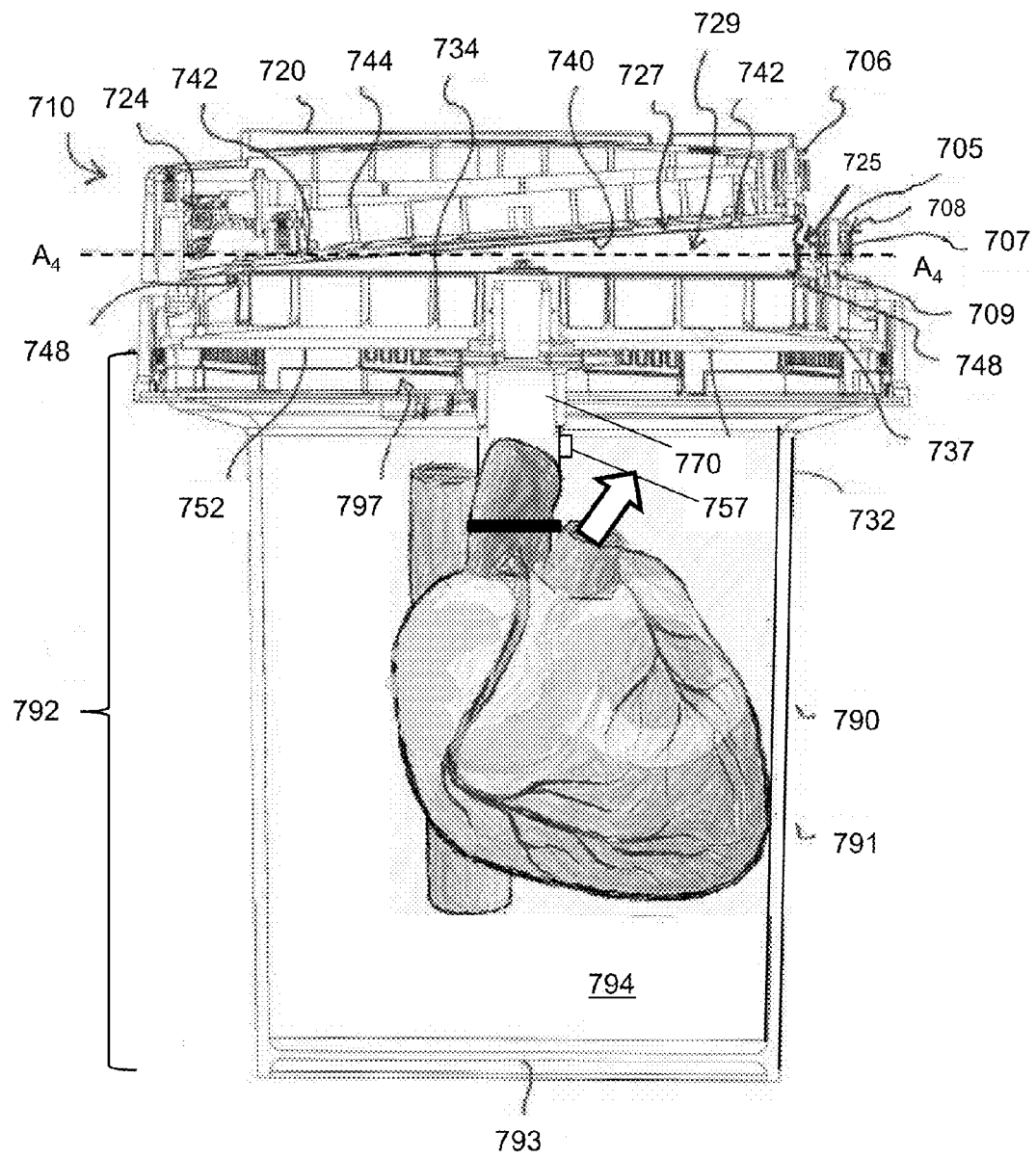
FIG. 6 is a schematic representation of a donor heart suspended in a first transport container and being perfused with oxygenated preservation solution.

In some versions of the invention, the preservation solution is circulated through the tissue using the tissue's cardiovascular system. For example, as shown in FIG. 6, the tissue may be an organ, e.g., a heart. The tissue can be coupled to the pumping chamber via an adapter, which is shown in FIG. 6 as lumen 770. Lumen 770 may be directly attached to the organ, e.g., via the vena cava, allowing oxygenated preservation solution to be perfused through the organ. A temperature sensor 757 may also be affixed to lumen 770 and be used to monitor the temperature of the preservation fluid in close proximity to the tissue. As shown by the arrow in FIG. 6, the perfused preservation fluid will exit the organ, e.g., via a pulmonary artery, and return to the storage chamber 792. The circulation of the preservation fluid, described above, will allow the preservation solution to be re-oxygenated prior to being re-perfused into the tissue. Additionally, using a first transport container such as shown in FIG. 6, perfusion pressure can also be varied, e.g., once per second, between a low and a high pressure, thereby simulating the natural pulsatile flow of blood through the vasculature of the tissues. This method of perfusion provides a more "natural" environment for absorption of oxygen and nutrients from the preservation solution, increases the amount of time that the organ can be transported, and improves the overall quality of the tissue upon arrival. Furthermore, because compressed oxygen is used to propel the pulsed circulation, the preservation fluid is reoxygenated throughout transport, replacing the oxygen that has been consumed by the tissue and displacing waste gases (i.e., $CO_2$). In some versions, a suite of sensors measures temperature, oxygen content, and pressure of the circulating fluids to assure that the tissue experiences a favorable environment during the entire transport.

Figure 7:
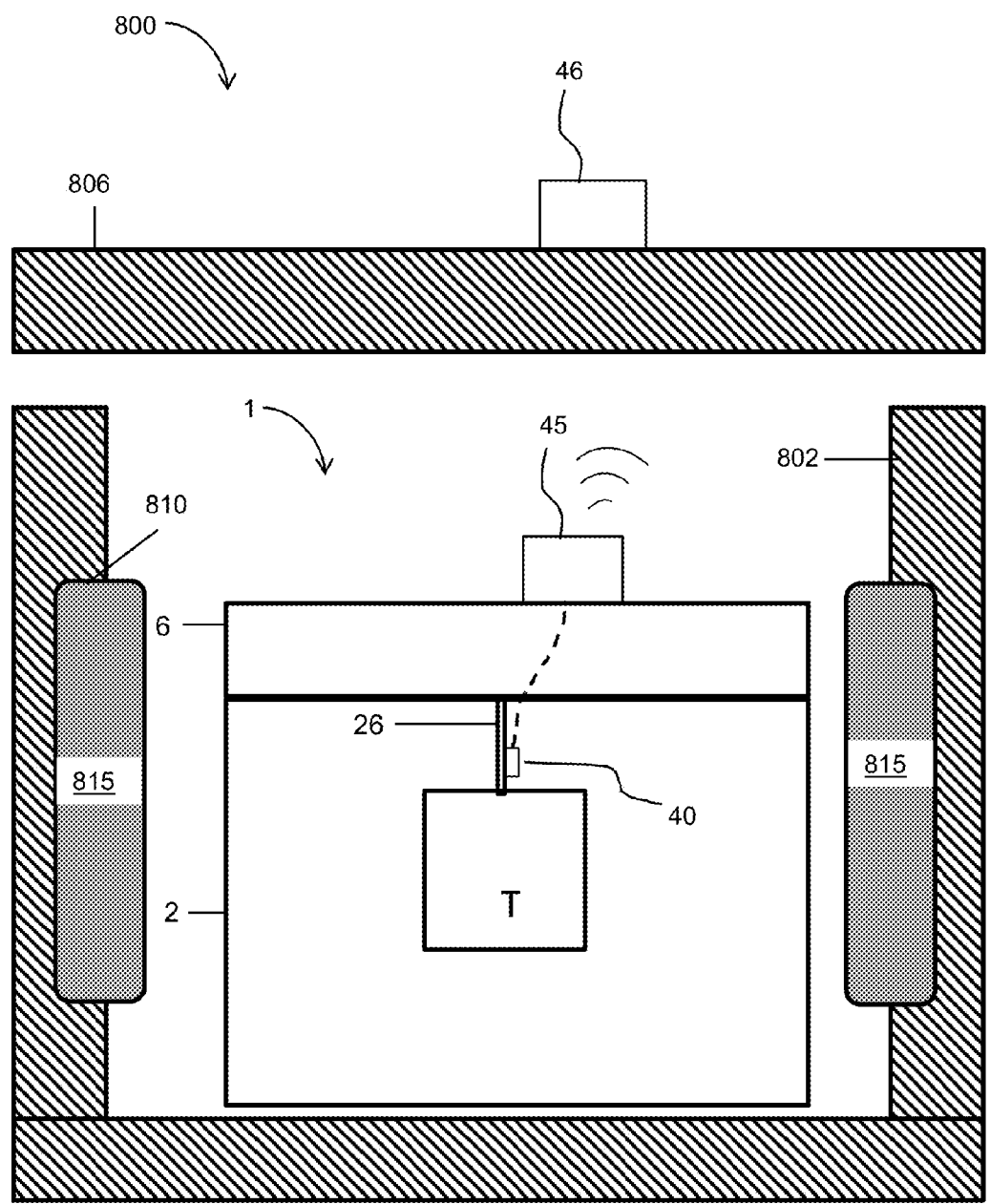
FIG. 7 shows an embodiment of a hypothermic transport system of the invention, including a first transport container, a second transport container, and cooling media for maintaining the temperature of the tissue being transported. The first transport container comprises a temperature sensor and a display, and the temperature can be wirelessly communicated to a second display on the exterior of the second transport container.

A complete system for hypothermic transport of tissues, comprising a static first transport container 1 and a second transport container 800 is shown in FIG. 7. The first static transport container comprises a storage vessel 2 and a lid without a pumping chamber 6, as described above with respect to FIG. 1. The second transport container 800 comprises an insulated vessel 802 and an insulated lid 806. The insulated vessel has at least one recess 810 configured to hold a cooling medium 815. As shown in FIG. 7, a sealed static first transport container 1 is placed in insulated vessel 802 along with cooling media 815, and the insulated lid is placed on insulated vessel 802 forming a temperature-regulated environment for transport of tissue.

The insulated vessel 802 and the insulated lid 806 will both comprise an insulating material that is effective in maintaining the temperature inside the second transport container 800. A suitable insulating material may be any of a number of rigid polymer foams with high R values, such as polystyrene foams (e.g. STYROFOAM™), polyurethane foams, polyvinyl chloride foams, poly(acrylonitrile)(butadiene)(styrene) foams, or polyisocyanurate foams. Other materials, such as spun fiberglass, cellulose, or vermiculite could also be used. Typically, the insulating vessel 802 will be constructed to provide a close fit for the first transport container, thereby affording additional mechanical protection to the first transport container and the tissues contained therein. In some embodiments, the insulated vessel 802 and the insulated lid 806 will be constructed of a closed-cell foam that will prevent absorption of liquids, for example water, body fluids, preservation fluid, saline, etc. While not shown in FIG. 7, the insulated vessel 802 and the insulated lid 806 may have a hard shell on the exterior to protect the insulating material from damage or puncture. The hard shell may be formed of metal (e.g. aluminum or steel) or of a durable rigid plastic (e.g. PVC or ABS). The hard shell may have antibacterial properties through the use of antibacterial coatings or by incorporation of metal that have innate antibacterial properties (e.g. silver or copper).

While not shown in FIG. 7, the insulated vessel 802 and the insulated lid 806 may be connected with a hinge, hasp, clasp, or other suitable connector. The second transport container 800 may include an insulating seal to make to make an air- or water-tight coupling between the insulated vessel 802 and the insulated lid 806. However, the insulated lid 806 need not be sealed to the insulated vessel 802 for the second transport container 800 to maintain a suitable temperature during transport. In some embodiments, the insulated vessel 802 and the insulated lid 806 will be coupled with a combination lock or a tamper-evident device. The insulated vessel 802 and/or the insulated lid 806 may additionally comprise a handle or a hand-hold or facilitate moving the second transport container 800 when loaded with a first transport container (static 1 or pulsatile 10). While not shown in FIG. 7, in some embodiments, insulated vessel 802 will additionally have external wheels (e.g. castor wheels or in-line skate type wheels). The insulated vessel 802 may also have a rollaboard-type retractable handle to facilitate moving the system between modes of transport or around a hospital or other medical facility.

In some embodiments, such as shown in FIG. 7, the second transport container 800 will comprise a second temperature display 46 which can display a temperature measured by the temperature sensor 40 to a user. The second temperature display 46 may receive measurements of temperature within the static first transport container 1 via a wired or a wireless connection. In the embodiment shown in FIG. 7, an electronics package on the lid 6 is coupled to the temperature display 45 and comprises a wireless transmitter that communicates with a receiver coupled to the second temperature display 46. This configuration avoids a user having to make a connection between the temperature sensor 40 and the second temperature display 46 after the first static transport container 1 has been placed in the insulated vessel. The second insulated transport container 800 may additionally comprise displays for additional relevant information, such as time since harvest, pressure inside the first transport container (static 1 or pulsatile 10), partial pressure of oxygen, or oxygen consumption rate of the biological sample.

Figure 8:
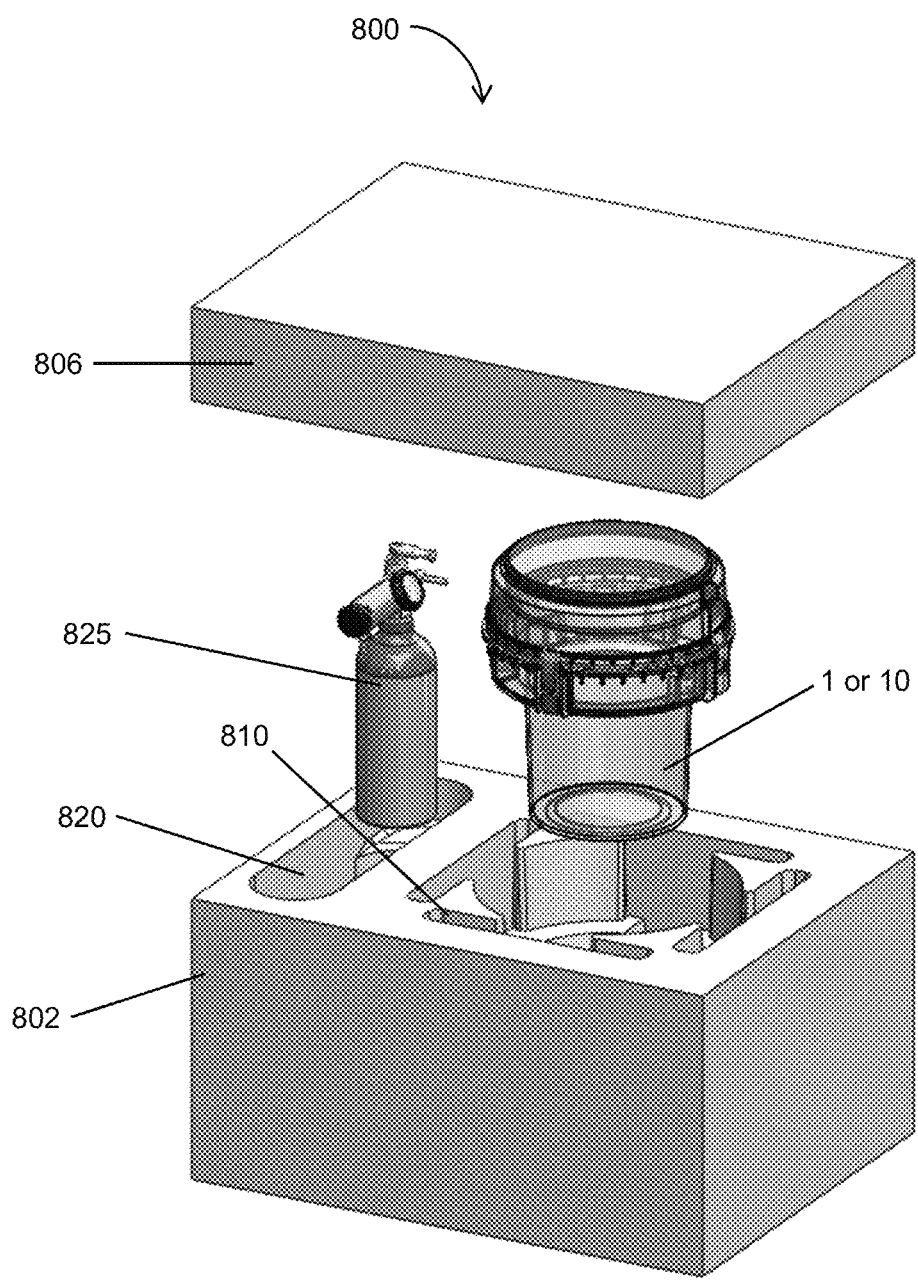
FIG. 8 shows an embodiment of a hypothermic transport system of the invention, including a first transport container, a second transport container, and recesses for holding cooling media for maintaining the temperature of the tissue being transported. The second transport container is also configured to transport a source of oxygen.

The system may use any of a number of cooling media 815 to maintain the temperature inside the second transport container 800 during transport. As shown in FIG. 7, the cooling media 815 may comprise eutectic cooling blocks, which have been engineered to have a stable temperature between 2-8° C., for example. The cooling media 815 will be arranged in recess 810 in the interior of the insulated vessel 802. The recess 810 may be a slot 825, such as shown in FIG. 8, or the recess may be a press-fit, or the cooling media 815 may be coupled to the walls of the insulated vessel 802 using a snap, screw, hook and loop, or another suitable connector. Eutectic cooling media suitable for use with the invention is available from TCP Reliable Inc. Edison, N.J. 08837, as well as other suppliers. Other media, such as containerized water, containerized water-alcohol mixtures, or containerized water-glycol mixtures may also be used. The container need not be rigid, for example the cooling media may be contained in a bag which is placed in the recess 810. Using the cooling media 815, e.g. eutectic cooling blocks, the invention is capable of maintaining the temperature of the sample in the range of 2-8° C. for at least 60 minutes, e.g., for greater than 4 hours, for greater than 8 hours, for greater than 12 hours, or for greater than 16 hours.

FIG. 8 shows another embodiment of a complete system for hypothermic transport of tissues, comprising a first transport container (1 or 10) and a second transport container 800. As in FIG. 7, the second transport container comprises an insulated vessel 802 and an insulated lid 806. The insulated vessel has recesses 810 for holding cooling media 815. As shown in greater detail in FIG. 9, the insulated vessel is formed to closely fit the first transport container (1 or 10) to provide mechanical protection to the container and to assure that the container remains upright during transport. The insulated vessel 802 and the insulated lid 806 have hard sides for durability, and may have wheels (not shown) for ease of transport. As shown in FIG. 8, the insulated vessel 802 additionally comprises an oxygenate recess 820 for holding a compressed oxygenate 825, for example a cylinder of compressed oxygen. As discussed in greater detail above, the compressed oxygenate can serve a dual purpose of oxygenating the preservation solution and also providing pressure to circulate the preservation solution around or through the tissue. While not shown in FIG. 8, second transport container 800 may additionally comprise a regulator and tubing to connect the compressed oxygenate to the first transport container (1 or 10).

Figure 9:
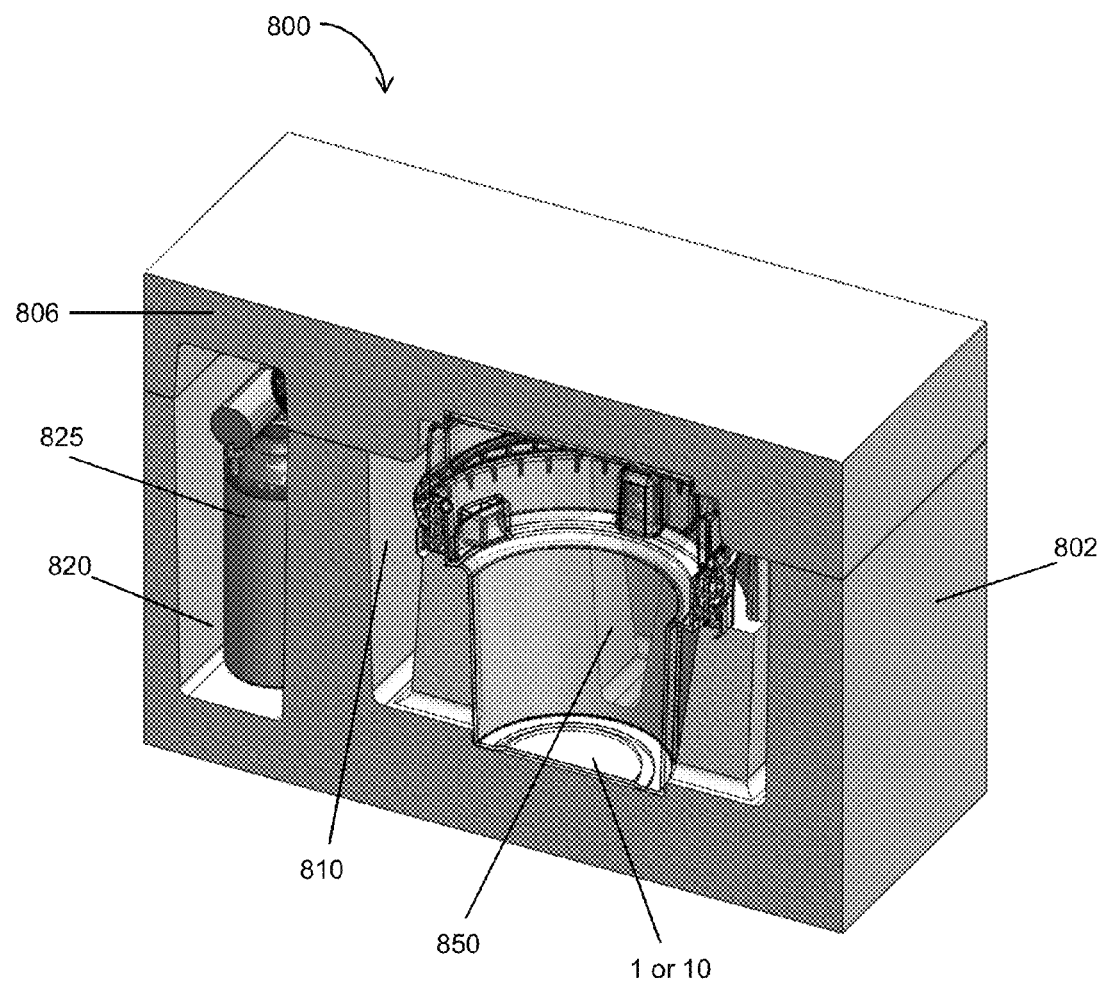
FIG. 9 shows a cut-away view of a hypothermic transport system of the invention, with detail of the interior structures that provide additional mechanical protection to the first transport container and its contents.

As shown in the cut-away view of the second transport container 800 in FIG. 9, both the insulated vessel 802 and the insulated lid 806 are designed to snugly fit the first transport container (1 or 10) to provide additional mechanical stability. While not visible in FIG. 9, the oxygenate recess 820 also provides a snug fit for the compressed oxygenate, which may be, for example, a size 4 cylinder of compressed gas. Also, as shown in FIG. 9, a thermal communication passage 850 may be provided (behind wall of first transport container) to allow better thermal flow between the cooling media 815 and the first transport container (1 or 10). In some instances, the interstitial space between the cooling media 815 and the first transport container 1 or 10 will be filled with a thermal transport fluid, such as water or an aqueous solution. In other instances, the interstitial space will be filled with air or another gas (e.g. dry nitrogen).

The disclosed systems provide a better option for transporting biological samples than the "picnic cooler" method. In one embodiment a medical professional will provide a hypothermic transport system of the invention, for example as shown in FIGS. 7-9, suspend a biological sample in preservation fluid within a first transport container, for example as shown in FIGS. 1-3, and maintain the temperature of the preservation fluid between 2 and 8° C. for at least 60 minutes. Because the first transport container has a temperature sensor and a temperature display, it will be possible for the medical professional to monitor the temperature of the sample after it has been sealed inside the first transport container. Such temperature information will be critical in evaluating the status of the sample during transport and for identifying failures during transport. In embodiments having a second display on the second transport container, it will be possible to monitor the temperature of the sample without opening the second transport container, thereby maintaining the hypothermic environment within.

Using the systems of the invention, the preservation fluid may be maintained at a pressure greater than atmospheric pressure, and may be oxygenated, for example by an accompanying cylinder of compressed oxygen, i.e., as shown in FIG. 8. In some instances, the preservation fluid will be circulated around tissue suspended in the first transport container, or the preservation fluid may be perfused through an organ suspended in the first transport container. Preferably, an organ will be perfused with preservation solution by using oscillating pressures, thereby simulating the systolic and diastolic pressures experienced by circulatory system of the organ in the body. When body fluids are transported, the body fluids may be transported by suspending a third container (e.g., a blood bag) within the first transport container.

Thus, using the system for hypothermic transport of tissues of the invention, it is possible to transport a biological sample (e.g. tissue, organs, or body fluids) over distances while maintaining a temperature of 2-8° C. Systems of the invention will enable medical professionals to keep tissues (e.g. organs) in a favorable hypothermic environment for extended periods of time, thereby allowing more time between harvest and transplant. As a result of the invention, a greater number of donor organs will be available thereby saving lives.

Additional system and method of the invention are disclosed in the Examples below, which should not be viewed as limiting the invention in any way.

EXAMPLE

Example 1

Viability of Hypothermicly Stored Kidneys with and without Perfusion

The benefits of pulsatile cold tissue storage over static cold tissue storage were evaluated in canines. Both methods of storage were compared to freshly harvested organs.

Kidney Harvest

Adult canines weighing about 25 to 30 kg were anesthetized with 25 ml/kg of sodium pentobarbital by an intravenous injection. The subject animals were intubated and ventilated with 40% oxygen to maintain normal arterial blood oxygenation. Subject animals were then placed in a supine position and a midline incision was made in the lower abdominal cavity so that both kidneys were exposed. Following heparinization, catheters were inserted into the descending aorta above, and the inferior vena cava just below the kidneys. The aorta and inferior vena cava were crossed clamped above and below the catheters and an infusion of cold University of Wisconsin Solution (UWS) at 4° C. was initiated. Infusions continued until all blood was cleared from the organ. During infusion, cold saline, at 4° C., was poured over the kidneys and the excess removed by suction. The aorta and inferior vena cava were ligated at the cross clamp and then cut, as were the ureters. The kidneys were quickly dissected free and placed on ice for catheterization of the ureters. The ureters were catheterized with a 2 inch 18 gage catheters. The aorta was also catheterized.

Static Storage

Four canine kidneys were attached via aortic catheter to an adapter coupled to the lid of a first transport container. The transport container additionally included a basket designed to support the organs. The organs were immersed into cold (4° C.) freshly prepared University of Wisconsin Solution (preservation solution). While the first transport container was capable of supplying pulsatile preservation solution, it was not used. That is, the kidneys were stored statically. The first transport container was then placed into an insulated transport case into which eutectic cold packs had been previously placed. Temperature was continuously monitored during 24 hours of storage. The average temperature during storage was 4.5° C.

Pulsatile Storage

Four canine kidneys were attached via aortic catheter to an adapter coupled to the lid of a first transport container. The aortic catheters were attached to the adapter so that that the aorta could receive pressurized preservation solution. The transport container additionally included a basket designed to support the organs. The organs were then immersed into cold (4° C.) freshly prepared University of Wisconsin Solution (preservation solution). The first transport container was pressurized with 100% $O_2$ at 2.5 to 3.0 psi and set to perfuse the kidneys at 70 pulses/min. Temperature and perfusion pressure were continuously monitored. The partial pressure of oxygen ($pO_2$) in the flowing preservation solution was measured at 15 minute intervals, both into and out of the organ. The average temperature during storage was 5.0° C.; the average perfusion pressure was 16.0 mmHg; the average preservation solution flow was 37.8 ml/min, the average $O_2$ delivery was 1.2 ml/min; the average $O_2$ consumption was 0.29 ml/min; and the average Renal Vascular Resistance (RVR; perfusion pressure×flow) was 0.43 mmHg/ml/min.

Evaluation of Kidney Viability

Following the preservation period, the kidneys were removed from the preservation device and connected to a Langendorff device to evaluate kidney function. Four additional kidneys were harvested and evaluated with the Langendorff device as a control. Each kidney were perfused with a 50:50 mixture of warm (37° C.) oxygenated (100% $O_2$) K—H solution containing inulin (15 mg/100 ml) and autologous blood. Perfusion was initiated slowly and incremented at 5 minute intervals until a mean arterial pressure of 150 mmHg was achieved. Urine, arterial and venous samples were collected from each kidney after 90 minutes in triplicate for inulin clearance and urine output measurement. Inulin was measured using the method of Waser as modified by Brown and Nolph. See Brown and Nolph, "Chemical measurements of inulin concentrations in peritoneal dialysis solution," *Clin. Chim. Acta,* 1977; 76: 103-12, incorporated herein by reference. The partial pressure of oxygen in the blood/K—H perfusate entering the renal arteries and exiting the renal veins was measured on a TruPoint Irma™ blood gas machine. Organ perfusion was measured by collecting the outflow from the renal veins during a 15 second time interval and corrected to flow/minute. Renal vascular resistance was calculated by dividing the perfusion pressure measured at the renal artery by the renal vein outflow in ml/min. Glomerular Filtration Rate (GFR) was calculated as the product of the urine inulin concentration and urine flow divided by the arterial plasma inulin concentration.

Figure 10:
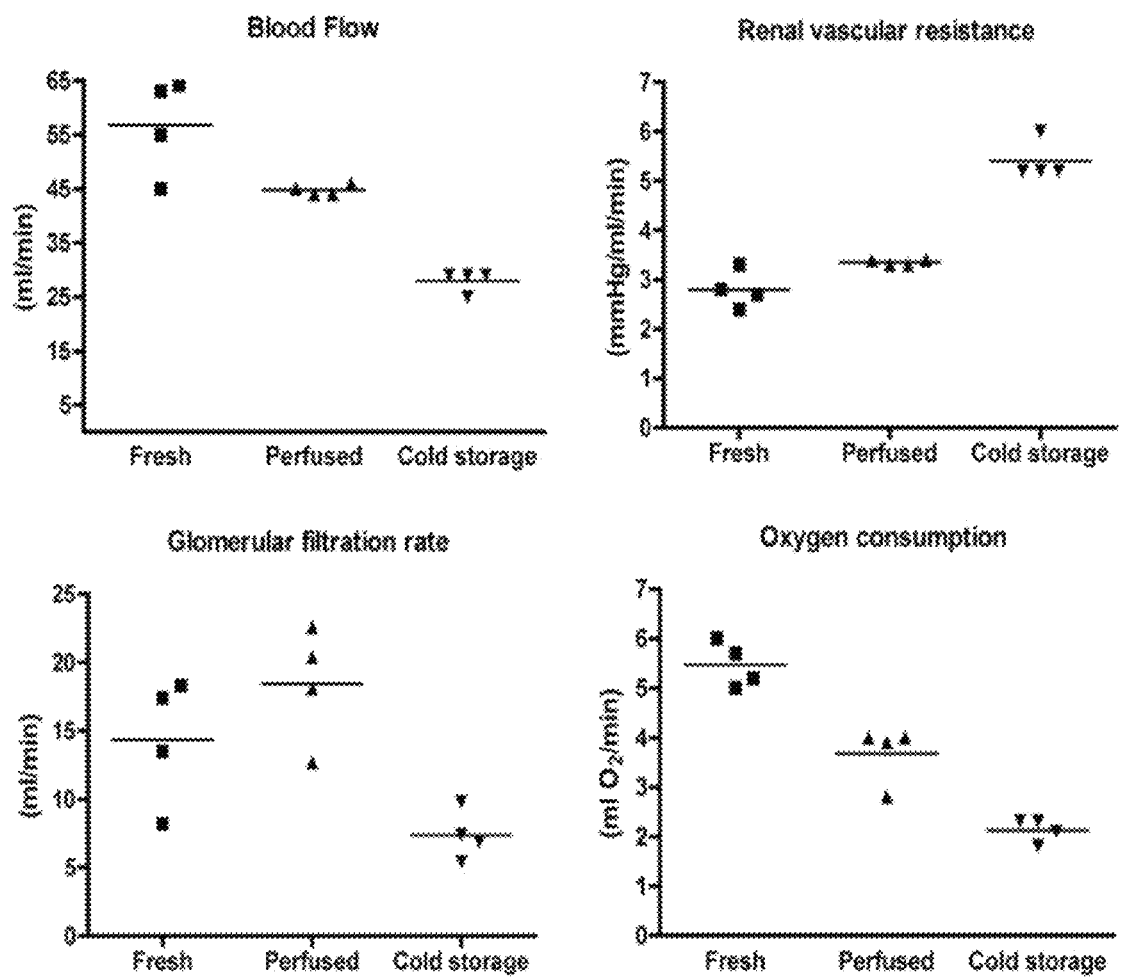
FIG. 10 shows measurements of blood flow, renal vascular resistance, glomerular filtration rate and oxygen consumption for fresh canine kidneys (■), canine kidneys hypothermicaly stored for 24 hours with perfusion (▲), and canine kidneys hypothermicly stored for 24 hours without perfusion (▼).

The results of the Langendorff measurements are shown graphically in FIG. 10. The temperature during function measurements on the Langendorff was 37.0±0.1° C. for all kidneys. Perfusion pressure for all kidneys was set at 150 mmHg. Renal vascular resistance (average) for freshly recovered kidneys was 2.8±0.4 mmHg/ml/min, 3.4±0.1 mmHg/ml/min for pulsatile stored kidneys, and 5.4±0.4 mmHg/ml/min for static stored kidneys. The RVR differences between the freshly recovered and pulsatile stored kidneys were not statistically significant, but the statically stored kidneys demonstrated a statistically higher RVR ($p<0.05$) (See FIG. 10).

Oxygen consumption (average) during testing by freshly recovered kidneys was 5.5±0.4 ml $O_2$/min, 3.7±0.6 ml $O_2$/min by pulsatile stored preserved kidneys, and 2.1±0.3 ml $O_2$/min by statically stored kidneys. GFR (average) was 14.3±4.6 ml/g/min for the freshly recovered kidneys, 18.4±4.3 ml/min for the pulsatile preserved organs, and 7.4±1.8 ml/min for the statically stored organs.

Looking at the results of FIG. 10, there was a statistical difference ($p<0.05$) between freshly-recovered and pulsatile stored kidneys in oxygen consumption but no statistical difference in GFR. Additionally, while blood flow and RVR were, on average, worse in the pulsatile storage kidneys as compared to the freshly recovered kidneys, the average for the pulsatile storage kidneys was within the range of the fresh kidneys. The data suggest that kidneys may be stored and/or transported for up to 24 hours using cold pulsatile storage without a substantial decrease in functionality.

In contrast, the static storage kidneys fared worse than both the fresh kidneys and the pulsatile storage kidneys in all aspects. In particular the static stored kidneys showed a significantly lower ($p<0.05$) oxygen consumption and GFR than either freshly recovered or pulsatile stored preservation groups, with a marked increase in RVR (See FIG. 10).

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A system for hypothermic transport of a biological sample, comprising:
    a first transport container comprising:
        a pumping chamber having a substantially planar semi-permeable membrane disposed at an inclined angle with respect to horizontal when the first transport container is placed on a horizontal surface, the semi-permeable membrane being configured to push against a fluid and cause the fluid to circulate inside said first transport container;
        an organ storage chamber configured to transport a biological sample;
        a fill port connected to an exterior of the first transport container and extending to the organ storage chamber;
        a vent port connected to the exterior of the first transport container and extending to the pumping chamber;
        a temperature sensor; and
        a temperature display; and
    a second transport container comprising an insulated cavity for receiving said first transport container and having recesses for receiving cooling media.

2. The system of claim 1, further comprising an oxygen source operably coupled to said first transport container.

3. The system of claim 2, wherein said oxygen source is a compressed gas cylinder.

4. The system of claim 2, wherein said oxygen source is in fluid communication with a first side of said semi-permeable membrane and configured to provide a force against said semi-permeable membrane, thereby causing a second side of said semi-permeable membrane to push against the fluid and cause the fluid to circulate inside said first transport container.

5. The system of claim 1, wherein said cooling media comprises eutectic cooling packs.

6. The system of claim 1, wherein said biological sample comprises tissues or organs.

7. The system of claim 1, wherein said biological sample is a container holding body fluids.

8. The system of claim 1, wherein said second transport container comprises a second temperature display in communication with said temperature sensor.

9. The system of claim 8, wherein said second temperature display communicates with said temperature sensor wirelessly.

10. The system of claim 1, wherein said first transport container additionally comprises a pressure sensor.

11. The system of claim 10, wherein said first transport container additionally comprises a pressure display operably coupled to said pressure sensor.

12. The system of claim 1, wherein said first transport container additionally comprises an oxygen sensor capable of measuring a partial pressure of oxygen in a fluid within said first transport container.

13. The system of claim 12, wherein said first transport container additionally comprises an oxygen display operably coupled to said oxygen sensor.

14. The system of claim 1, wherein the system is capable of maintaining a temperature of said fluid inside said first transport container of between 2° C. and 8° C. for at least 4 hours with the use of eutectic cooling media.

15. The system of claim 1, wherein the vent port is connected to the pumping chamber adjacent to a highest point of the inclined membrane.

16. The system of claim 1, wherein the semi-permeable membrane is inclined at an angle between approximately 1°-10° with respect to horizontal.

17. The system of claim 1, wherein said fluid is a preservation fluid.

18. The system of claim 1, further comprising an adapter configured to couple the biological sample to the pumping chamber.

19. The system of claim 1, further comprising a valve in communication with the organ storage container and the pumping chamber.

20. The system of claim 19, wherein the valve is a ball check valve.

* * * * *